United States Patent
Schuhrke et al.

(10) Patent No.: US 8,662,667 B2
(45) Date of Patent: Mar. 4, 2014

(54) OPHTHALMOLOGIC VISUALIZATION SYSTEM

(75) Inventors: Thomas Schuhrke, Munich (DE); Günter Meckes, Munich (DE); Stefan Gräber, Munich (DE); Keith Thornton, Puchheim (DE)

(73) Assignee: Carl Zeiss Meditec AG, Jena (DE)

( * ) Notice: Subject to any disclaimer, the term of this patent is extended or adjusted under 35 U.S.C. 154(b) by 577 days.

(21) Appl. No.: 12/801,689

(22) Filed: Jun. 21, 2010

(65) Prior Publication Data

US 2011/0019150 A1     Jan. 27, 2011

Related U.S. Application Data

(63) Continuation of application No. PCT/EP2008/068102, filed on Dec. 19, 2008, and a continuation-in-part of application No. PCT/EP2008/068103, filed on Dec. 19, 2008, and a continuation-in-part of application No. PCT/EP2008/068104, filed on Dec. 19, 2008, and a continuation-in-part of application No. PCT/EP2008/068107, filed on Dec. 19, 2008, and a continuation-in-part of application No. PCT/EP2008/068108, filed on Dec. 19, 2008.

(60) Provisional application No. 61/213,608, filed on Jun. 24, 2009.

(30) Foreign Application Priority Data

| Dec. 21, 2007 | (DE) | 10 2007 055 919 |
|---|---|---|
| Dec. 21, 2007 | (DE) | 10 2007 055 921 |
| Dec. 21, 2007 | (DE) | 10 2007 055 922 |
| Dec. 21, 2007 | (DE) | 10 2007 055 923 |
| Dec. 21, 2007 | (DE) | 10 2007 055 924 |

(51) Int. Cl.
  *A61B 3/14*     (2006.01)

(52) U.S. Cl.
  USPC .......................... 351/206; 351/209

(58) Field of Classification Search
  USPC ........................... 351/206, 209, 210
  See application file for complete search history.

(56) References Cited

U.S. PATENT DOCUMENTS

| 5,070,883 A | 12/1991 | Kasahara |
| 6,030,080 A | 2/2000 | Ohman |

(Continued)

FOREIGN PATENT DOCUMENTS

| DE | 102 97 574 T5 | 4/2005 |
| DE | 20 2005 019 715 U1 | 2/2006 |

(Continued)

OTHER PUBLICATIONS

Daugman, J., "How Iris Recognition Works", IEEE Transactions on Circuits and Systems for Video Technology, vol. 14, No. 1, 2004, pp. 21 to 30.

(Continued)

*Primary Examiner* — Mahidere Sahle
(74) *Attorney, Agent, or Firm* — Walter Ottesen P.A.

(57) ABSTRACT

A method determines the position and/or radius of the limbus and/or the position and/or radius of the pupil of a patient eye. In the method, an image of the patient eye is obtained and a plurality of different ring-shaped comparison objects having respective radii and respective centers are provided. The image is correlated with the plurality of comparison objects to yield a local best match between the image and the comparison objects when there is a coincidence of one of the ring-shaped comparison objects and a ring-shaped jump in brightness in the image having the same radius and the same center. The comparison objects having a local best match with the image are determined. Thereafter, the position of the center of the comparison object having a local best match with the image is selected as the position of the center of the limbus and/or the position of the center of the pupil.

11 Claims, 13 Drawing Sheets

(56) References Cited

U.S. PATENT DOCUMENTS

| | | |
|---|---|---|
| 6,204,858 B1 | 3/2001 | Gupta |
| 6,254,046 B1 | 7/2001 | Biber |
| 6,322,216 B1 | 11/2001 | Yee et al. |
| 6,556,853 B1 | 4/2003 | Cabib et al. |
| 6,830,334 B2 | 12/2004 | Niven et al. |
| 7,044,602 B2 | 5/2006 | Chernyak |
| 7,261,415 B2 | 8/2007 | Chernyak |
| 7,284,858 B2 | 10/2007 | Bergner et al. |
| 7,467,869 B2 | 12/2008 | Kahlen |
| 7,699,468 B2 | 4/2010 | Gaida |
| 2003/0108225 A1 | 6/2003 | Li |
| 2003/0181803 A1 | 9/2003 | Sander |
| 2004/0102799 A1 | 5/2004 | Perez et al. |
| 2004/0143244 A1 | 7/2004 | Gray et al. |
| 2005/0110947 A1 | 5/2005 | Chaduc |
| 2006/0044509 A1 | 3/2006 | Fluegge et al. |
| 2006/0116668 A1 | 6/2006 | Gray et al. |
| 2006/0228011 A1 | 10/2006 | Everett et al. |
| 2006/0247659 A1 | 11/2006 | Moeller et al. |
| 2007/0171363 A1 | 7/2007 | Chen et al. |
| 2008/0252849 A1 | 10/2008 | Van Saarloos |

FOREIGN PATENT DOCUMENTS

| | | |
|---|---|---|
| DE | 20 2005 021 156 U1 | 4/2007 |
| DE | 10 2005 055 058 A1 | 5/2007 |
| DE | 600 30 995 T2 | 6/2007 |
| DE | 10 2007 055 919 A1 | 6/2009 |
| DE | 10 2007 055 921 A1 | 6/2009 |
| DE | 10 2007 055 922 A1 | 6/2009 |
| DE | 10 2007 055 923 A1 | 6/2009 |
| DE | 10 2007 055 924 A1 | 6/2009 |
| WO | WO 2007/085682 | 8/2007 |
| WO | WO 2009/080789 A1 | 7/2009 |
| WO | WO 2009/080790 A1 | 7/2009 |
| WO | WO 2009/080791 A1 | 7/2009 |
| WO | WO 2009/080792 A1 | 7/2009 |
| WO | WO 2009/080793 A1 | 7/2009 |

OTHER PUBLICATIONS

Heishman, R. et al, "Pupils—Enabling a Dialogue Between the Machine and the Brain", IEEE, 2001, pp. 87 to 93.

Ivins, J. et al, "A deformable model of the human ins for measuring small three-dimensional eye movements", Machine Vision and Applications (1998) 11: pp. 42 to 51.

Leimberg, D. et al, "Heuristics for speeding up gaze estimation", XP-008063327.

Newman, R. et al, "Real-Time Stereo Tracking for Head Pose and Gaze Estimation", IEEE, 2000, pp. 122 to 128.

Perez, C. et al, "Log-Linear Elliptic Transform for Frontal-Face Parameter Estimation", IEEE, 2007, pp. 1130 to 1134.

Smolka, B. et al, "Towards automatic redeye effect removal", Pattern Recognition Letters 24 (2003), pp. 1767 to 1785, Elsevier Science B.V.

Song, J. et al, "A robust eye detection method using combined binary edge and intensity information", Pattern Recognition 39 (2006), pp. 1110 to 1125, Elsevier Ltd.

Toennies, K. et al, "Feasibility of Hough-Transform-Based Iris Localisation for Real-Time-Application", IEEE, 2002, pp. 1053 to 1058.

Yuille, A. et al, "Feature Extraction from Faces Using Deformable Templates", International Journal of Computer Vision, 1992, 8:2, pp. 99 to 111.

OPHTHALMOLOGIC VISUALIZATION SYSTEM

CROSS REFERENCE TO RELATED APPLICATIONS

This application is a continuation-in-part application which claims priority of U.S. provisional application Ser. No. 61/213,608, filed Jun. 24, 2009, and also is a continuation-in-part application which claims priority of the following international patent application nos.: (a) PCT/EP 2008/068102; (b) PCT/EP 2008/068103; (c) PCT/EP 2008/068104; (d) PCT/EP 2008/068107; and, (e) PCT/EP 2008/068108, all filed Dec. 19, 2008, designating the United States and claiming priority from the following application nos.: (a) DE i0 2007 055 923.4; (b) DE i0 2007 055 924.2; (c) DE i0 2007 055 922.6; (d) DE i0 2007 055 921.8; and, (e) DE i0 2007 055 919.6, respectively, all filed Dec. 21, 2007, and the entire contents of all of the above applications are incorporated herein by reference.

FIELD OF THE INVENTION

The invention relates to an opthalmologic visualization system as well as a method for determining the position of the limbus or the pupil and/or radius of the limbus or the radius of the pupil of the eye of a patient.

BACKGROUND OF THE INVENTION

In opthalmologic surgery, it is important for a surgeon to have precise knowledge of the size and position of characteristic components of the patient eye, such as the size and position of the following: the iris, pupil or limbus.

In order to eliminate ametropia, for example, via laser ablation of the cornea (LASIK), a surgeon must know where the penetration point of the vision axis through the cornea of the patient eye lies. The surgeon should know precisely the position of this point also during a surgical procedure.

In cataract surgery, the position of the surgical incisions is important which the surgeon undertakes in the patient eye. Here, the natural lens of the human eye, in which a cataract has developed, is replaced by an artificial lens. For this purpose, the surgeon prepares an opening in the region of the limbus through the sclera or the cornea close to the iris. The patient eye can move during this procedure. Also, blood from injured blood vessels can cover the structures of characteristic components of the patient eye. For a surgeon, it is then difficult to find the correct location for surgical incisions in the patient eye.

SUMMARY OF THE INVENTION

It is an object of the invention to determine the position and/or the radius of the limbus and/or the position and/or the radius of the pupil of the patient eye in that an image of the patient eye is correlated with a plurality of different ring-shaped comparison objects which have a radius and a center in such a manner that a local best match results between the image of the patient eye and the comparison objects when there is a coincidence of a ring-shaped comparison object with a ring-shaped jump in brightness in the image of the patient eye having the same radius and the same center. The comparison objects are determined having an at least local best match with the image. The position of the center of the comparison object having an at least local best match with the image of the patient eye is then selected as the position of the center of the limbus and/or the position of the center of the pupil. The radius of the comparison object with the at least local best match with the image of the patient eye is selected as the radius of the limbus and/or as the radius of the pupil.

Preferably, the radii of the comparison objects, which are applied for the comparison, are different at first. The radius of the comparison object, which has the largest radius and has a largest local best match between the image of the patient eye and the comparison objects, is then selected as the radius of the limbus. The radius of the comparison object, which has the second largest radius and has the at least local best match between the image of the patient eye and the comparison object, corresponds to the radius of the pupil. The center of the comparison object, which has the largest radius and has the at least local best match between the image of the patient eye and the comparison objects, corresponds to the position of the center of the limbus. The center of the comparison object, which has the second largest radius and the at least local best match between the image of the patient eye and the comparison object, is selected as the position of the center of the pupil.

When the radius of the limbus or of the pupil of a patient eye is known, the radius of the ring-shaped comparison objects can all be the same for the detection of the position of the center of the limbus or of the pupil of the patient eye.

It is advantageous when the red color component, which corresponds to the red color channel, of a digital image of a patient eye forms the basis of the correlation of the ring-shaped comparison objects with the image of the patient eye.

For a comparison with the image of the patient eye, a ring-shaped comparison object from the plurality of ring-shaped comparison objects can have two concentric ring-shaped components. The ring-shaped comparison object can also be a polygon. Especially, a corresponding ring-shaped comparison object can also have segments. It is advantageous to configure the comparison object as a ring and the ring-shaped comparison object can especially be configured as a disc. A ring-shaped comparison object can, especially, be a part ring. The part ring is a ring wherein an arcuate segment of the ring is omitted.

It is especially advantageous when a digital image of the patient eye is correlated in its edge region with a ring-shaped comparison object configured as a part ring.

Ring-shaped comparison objects in the form of closed or part ring filters are advantageous. For these ring filters, the filter response of the ring filters can be computed for the image of the patient eye as a measure for the correlation of the image of the patient eye and the ring filters. Preferably, the ring filters have an inner filter ring and an outer filter ring. The inner and outer filter rings of the ring filters each contribute with a different sign to the filter response. An at least local maximum filter response is determined for the ring filters. The position of the center and the radius of the ring filter which forms the basis of the filter response can then be selected as the position of the center of the limbus of the patient eye and as the radius of the limbus and/or as the position of the center of the pupil of the patient eye and the radius of the pupil.

In order to determine the center of the limbus, the radius of the inner filter ring is smaller than the radius of the limbus of the patient eye. The radius of the outer filter ring is greater than the radius of the limbus of the patient eye. For determining the center of the pupil, the radius of the inner filter ring is smaller than the radius of the pupil of the patient eye and the radius of the outer filter ring is greater than the radius of the pupil of the patient eye.

The filter response is computed in a computer unit by convolution of the digital image of the patient eye with a filter function for the ring filters. The computer unit determines a filter function with an at least local maximum filter response from the computed filter responses.

The radius of the ring filter having the at least local maximum filter response is then selected as the radius of the pupil or of the limbus of the patient eye. The position of the center of the ring filter is determined as the position of the center of the pupil or of the limbus of the patient eye.

It is advantageous to compare a measure for the correlation of the image of the patient eye and of the ring-shaped comparison object, which has the best match to the image of the patient eye, to a measure for the correlation of a reference image having a ring-shaped comparison object. When the ring-shaped comparison object is a ring filter, the criterion for the local best match to the image of the patient eye can be an at least local maximum filter response of one ring filter for the image of the patient eye and for the reference image.

From the deviation of the measure for the correlation of the image of the patient eye from the measure for the correlation of the reference image with the comparison object, a quantity can then be generated as a measure for the reliability of a determined radius of the pupil and/or of the limbus of the patient eye and/or of a determined position of the center of the pupil and/or of the limbus of the patient eye.

It is advantageous to indicate to a surgeon this measure for the reliability by means of a display unit. This indication can be acoustic or optical. The display can especially be reflected into the viewing beam path of an eye viewing system.

According to the invention, a digital image of the patient eye can be detected in order to convolute the detected image of the patient eye with the adjacent ring-shaped filters with mutually adjacent rings. These filters have different radii. Here, the difference of the filter responses of two different adjacent rings is formed in each case. Local maximum differences and the radii are determined corresponding to the filters having these differences. The smaller of the determined radii can then be determined as the radius of the pupil of the patient eye and/or the position of the center of the filter with the smaller radius can be determined as the position of the center of the pupil of the patient eye. The larger of the radii, which are determined for a maximum difference, is then determined as the radius of the limbus of the patient eye and/or the position of the center of the filter having the larger radius is determined as the position of the center of the limbus of the patient eye.

It is advantageous to determine a favorable radius for the ring-shaped comparison objects in order to determine the position of the center of the limbus of the patient eye and/or the position of the center of the pupil of the patient eye by a correlation of time sequentially detected digital images of the patient eye during an eye treatment with ring-shaped comparison objects having this favorable radius and a different center.

It is also advantageous when the determined favorable radius is automatically adapted when there is a change of the recording mode of a camera detecting digital images of the patient eye. The determined favorable radius can especially be a radius of a comparison object selected as the radius of the limbus or the radius of the pupil of the patient eye.

The invention is based on the realization that in the images of the eye, which are recorded in the context of a treatment of the eye, characteristic eye components such as the limbus or the pupil edge define ring-shaped transition objects of brightness transitions and that these components can be especially easily and reliably found based on the comparison with a corresponding comparison object or via the convolution with a corresponding ring-shaped filter especially while forming differences. The search for a ring-shaped transition object is extremely robust compared to impairments which can deteriorate a recording. These impairments are in the form of dominating images during a surgical procedure. When, for example, instruments partially cover the eye, further pronounced edges emerge which could cause intense difficulties with each edge detection method. Then, the edges of these instruments would be detected in lieu of the edges of the limbus or of the edges of the pupil. However, the structure of the limbus or the edge of the pupil in the image of a patient eye with surgical instruments is ring-shaped. Possibly, the structure of the limbus or the pupil is interrupted and, inter alia, also slightly deformed. The position and radius of the structure of the limbus and of the pupil can still be reliably found via correlation with ring-shaped comparison objects.

The invention extends also to a computer program for a method for determining the position of the limbus and/or the pupil of a patient eye. Furthermore, the invention also extends to an arrangement for determining the position and/or the radius of the limbus and/or of the pupil of a patient eye with a video camera for recording digital images of at least one section of the patient eye and with a computer unit which contains such a computer program.

The invention extends especially to an opthalmologic visualization system for eye surgery with an arrangement for determining the position and/or radius of the limbus and/or the position and/or radius of the pupil of a patient eye. In this system, an image of the patient eye is correlated in such a manner with a plurality of different ring-shaped comparison objects having respective radii and respective centers. This correlation is such that a local best match between the image of the patient eye and the comparison objects results when there is a coincidence of one of the ring-shaped comparison objects and a ring-shaped jump in brightness in the image of the patient eye having the same radius and the same center. With this system, the comparison objects having a local best match with the image are determined and the position of the center of the comparison object having a local best match with the image of the patient eye is selected as the position of the center of the limbus and/or the position of the center of the pupil.

The radius of the comparison object having the at least local best match with the image of the patient eye is selected as the radius of the limbus and/or as the radius of the pupil.

In the visualization system, (a) the radius of that comparison object, which has the largest radius and has a local best match between the image and the comparison objects, is selected as the radius of the limbus; and/or, (b) the radius of the comparison object having the second largest radius and having the local best match between the image and the comparison object is selected as the radius of the pupil; and/or, (c) the center of the comparison object having the largest radius and having the local best match between the image and the comparison objects is selected as the position of the center of the limbus; and/or, (d) the center of the comparison object having the second largest radius and having the local best match between the image and the comparison objects is selected as the position of the center of the pupil.

The radius of the ring-shaped comparison objects can also be equal in order to determine the center of the limbus or the pupil of the patient eye by means of the visualization system.

It is advantageous in the visualization system, when a red color component of a digital image of the patient eye, which corresponds to the red color channel, forms the basis of the correlation of the ring-shaped comparison objects with the image of the patient eye.

In the visualization system, the ring-shaped comparison objects can be closed ring filters or part ring filters having an inner filter ring and an outer filter ring. A visualization system is especially advantageous wherein a measure for the correlation of the image of the patient eye and of the comparison objects can be determined by computation of the filter response of a ring filter for the image of the patient eye. Here, it is favorable when the inner and outer filter rings of the ring filter each contribute with a different sign to the filter response.

Preferably, a comparison takes place in the ophthalmologic visualization system for the measure wherein a first measure for the correlation of the image of the patient eye and of the oomparison object in the form of the ring filter having an at least local maximum filter response is compared to a second measure for the correlation of a reference image and a comparison object in the form of a ring filter with an at least local maximum filter response; a quantity is generated from the deviation of the first measure from the second measure with the quantity being a measure for the reliability of a determined radius of the pupil or of the limbus of the patient eye or a determined position of the center of the pupil or of the limbus of the patient eye; and, the quantity is indicated by an indicating unit.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
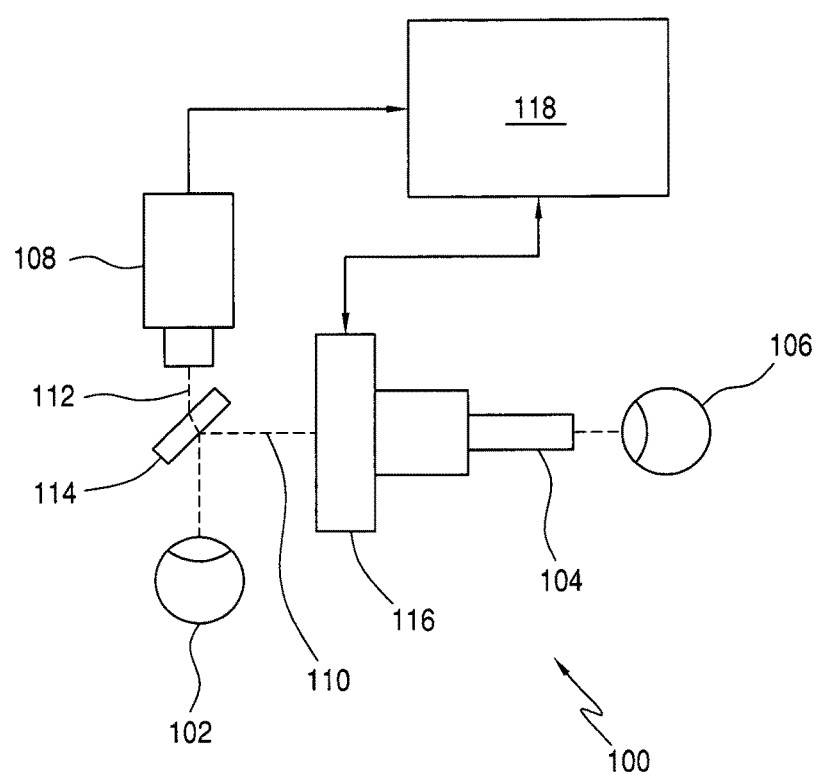
FIG. 1 is a schematic of an opthalmologic visualization system.

FIG. 1 shows an opthalmologic visualization system 100. The visualization system 100 is designed for viewing a patient eye 102. The visualization system 100 serves especially for the use in so-called cataract surgical procedures. In this surgical procedure, the natural lens of the eye of a patient is replaced by an artificial lens.

The visualization system 100 includes an imaging optic having an ocular 104. Via this imaging optic, a viewer such as a surgeon can view the patient eye 102 with a viewing eye 106. The visualization system 100 includes a video camera 108 with which digital images of the patient eye 102 can be recorded.

The imaging optic and the ocular 104 define an imaging beam path 110. The video camera 108 has an imaging beam path 112. A beam splitter 114 is arranged in the imaging beam path 110 of the imaging optic with the ocular 104 and in the imaging beam path 112 with the video camera 108. The beam splitter 114 permits the patient eye 102 to be viewed simultaneously with the video camera 108 and the imaging optic with the ocular 104.

The imaging optic with the ocular 104 includes a pattern generation unit 116. Auxiliary patterns can be generated with the pattern generation unit 116 and these auxiliary patterns are superposed on the image of the patient eye 102 visualized via the imaging optic. With such an auxiliary pattern, an optimal position of a surgical incision in a patient eye can be displayed to the surgeon via the imaging optic.

The pattern generation unit 116 is a projector having a ring-shaped LED-display. With the aid of the pattern generation unit 116, a pattern can be generated which is projected onto the patient eye 102 via the beam splitter 114. Also, other configurations are possible for the pattern generation unit 116.

The visualization system 100 includes a computer unit 118. The pattern generation unit 116 is connected to the computer unit 118 and the video camera 108 is also connected to the computer unit 118.

In the operation of the visualization system 100, the image data, which is recorded with the video camera 108, is transmitted to the computer unit 118. In the computer unit 118, these data are stored and analyzed. The computer unit 118 computes an auxiliary pattern with the aid of this data. This auxiliary pattern is projected onto the patient eye via the pattern generation unit 116.

The optimal position of a surgical incision in a patient eye is displayed to a surgeon during a cataract surgical procedure. To do this, the computer unit 118 determines the position and the radius of the limbus of the patient eye via image evaluation of the image of the patient eye 102 detected by the video camera 108. For this purpose, the computer unit 118 correlates an image of the patient eye 102 with ring-shaped comparison objects. The image of the patient eye 102 is detected by the video camera 108.

Figure 2:
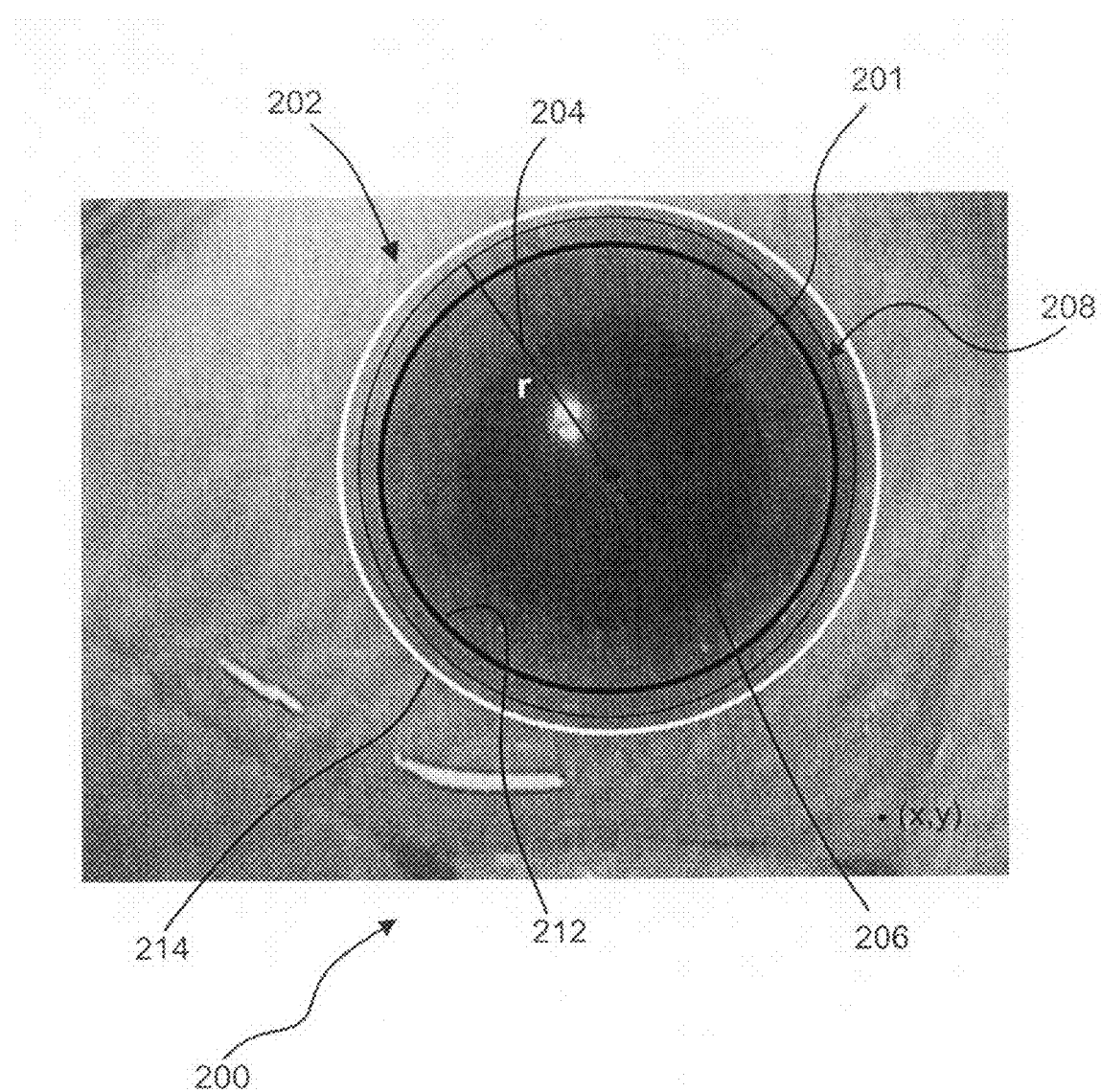
FIG. 2 shows the image of a patient eye with a ring filter.

FIG. 2 shows an image 200 of a section of a patient eye with a ring-shaped comparison object 202. The image 200 is detected by means of the video camera 108. The ring-shaped comparison object 202 has a radius 204 and a center 206. In the image 200, the center 206 of the comparison object 202 corresponds to the center of the limbus 208 of the patient eye in the image 200. The radius of the limbus 208 in the image 200 corresponds to the radius of the comparison object 202.

The image 200 of the patient eye has a jump in brightness in the region of the limbus 208. The region of the image starting directly at the limbus 208 and lying within the limbus 208 is darker than the region of the image starting at the limbus and lying outside of the limbus 208. The radius 204 and the center 206 of the comparison object 202 correspond to the radius and the center of the limbus 208. For this reason, the comparison object 202 is locally coincident with the image 200 of the patient eye. The comparison object 202 is correlated here with the image 200 of the patient eye.

The comparison object 202 is a ring filter. The ring filter 202 has two ring-shaped components, namely, an inner filter ring 212 and an outer filter ring 214. The filter ring 202 is made up of the inner filter ring 212 and the outer filter ring 214.

To determine the center and the radius of the limbus in an image 200 of a patient eye detected by the video camera 108, the computer unit 118 basically compares the image of the patient eye to a plurality of comparison objects which have different radii and a different center. Center and radius of the pupil 201 of the patient eye in the image 200 can be determined in a corresponding manner by comparison to a plurality of comparison objects which have different radii and different centers.

As a measure for the correlation of the image of the patient eye with a comparison object, the computer unit 118 computes the filter response of the comparison objects for the image of the patient eye by convoluting of ring filters with the image of the patient eye which ring filters correspond to the ring filter 202 in FIG. 2.

The computer unit 118 computes the correlation with the image of the patient eye for the ring filters. The ring filters are so standardized that the filter response for a gray surface yields the value zero. The contributions of the outer filter ring to the filter response of a ring filter have a positive sign. The sign of the contributions of the inner filter ring to the filter response of a ring filter is, in contrast, negative. The contributions of, the inner and of the outer filter rings to the filter response are therefore weighted. The ring filters for the determination of the correlation with the image of the patient eye can be closed or partially open. A filter ring, which is partially open, is a filter ring wherein an arcuate segment is missing. Also, signs noted above could also be opposite. Thus, the contributions of the outer filter ring could have a negative sign and the contributions of the inner filter ring could have a positive sign.

Figure 3:
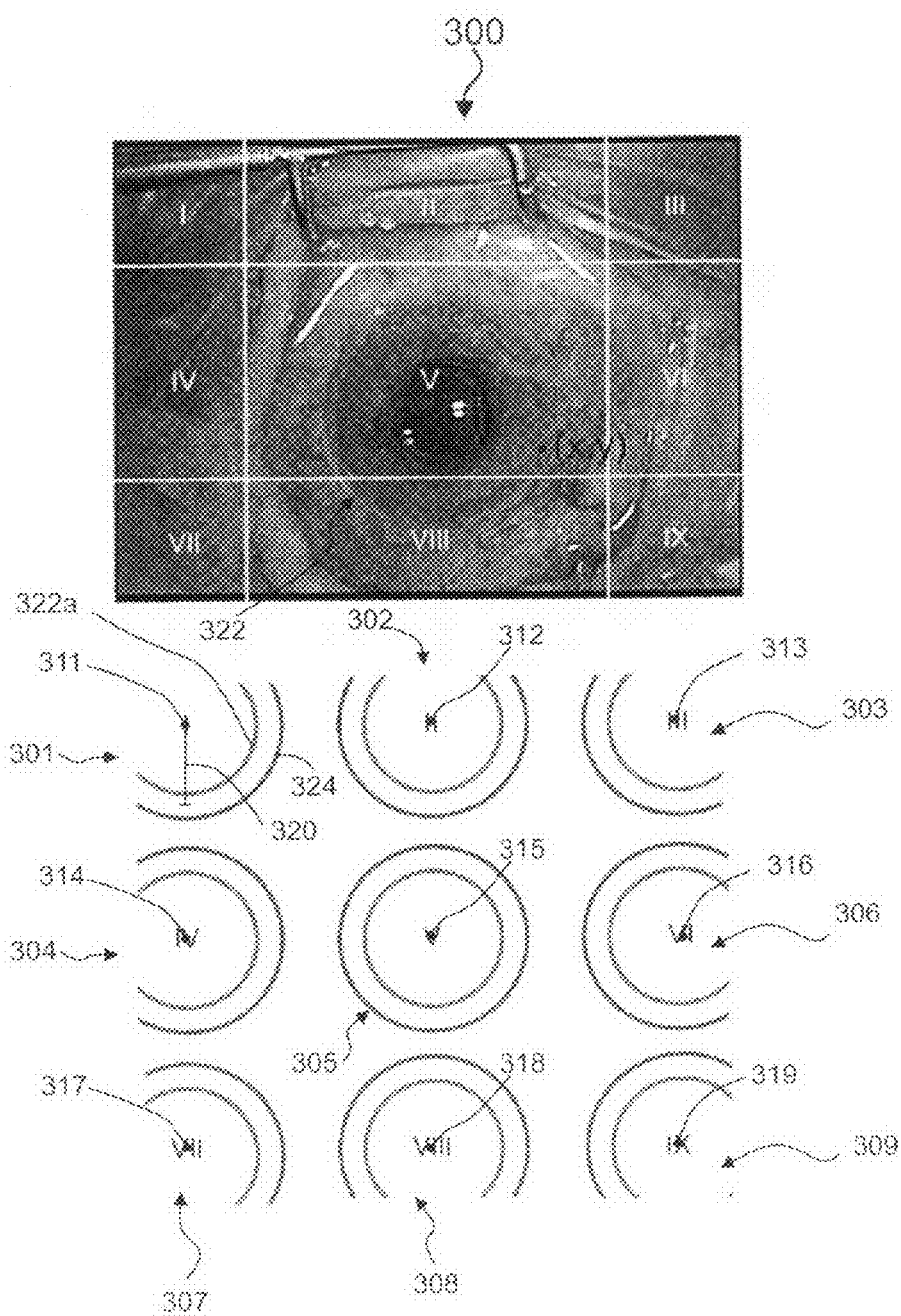
FIG. 3 shows a further image of a patient eye with a ring filter.

FIG. 3 shows a section of an image 300 of a patient eye and ring filters 301 to 309 which have different centers 311 to 319 but the same radius 320.

The ring filters 301 to 309 are each ring-shaped comparison objects having an inner filter ring 322a and an outer filter ring 324. The ring filter 305 is a closed ring-shaped comparison object. The ring filters 301 to 304 and 306 to 311 are ring-shaped comparison objects in the form of part rings.

By computing the filter response, the computer unit 118 compares the image of the patient eye, which was detected with the video camera 108, to ring filters which have different radii and different centers. The ring filters are open or closed depending upon their position with reference to the image of the patient eye. For example, the ring filter 301 is determined for the computation of a filter response in the section I of the image 300. The ring filter 302 is utilized in section II for the computation of the filter function. The ring filters 303 to 309 are applied for the computation of the filter function in the sections III to IX. These measures ensure that the center of the limbus 322 in the image 300 of a patient eye can be reliably detected even when the center of the limbus lies in the edge region of the image.

Figure 4:
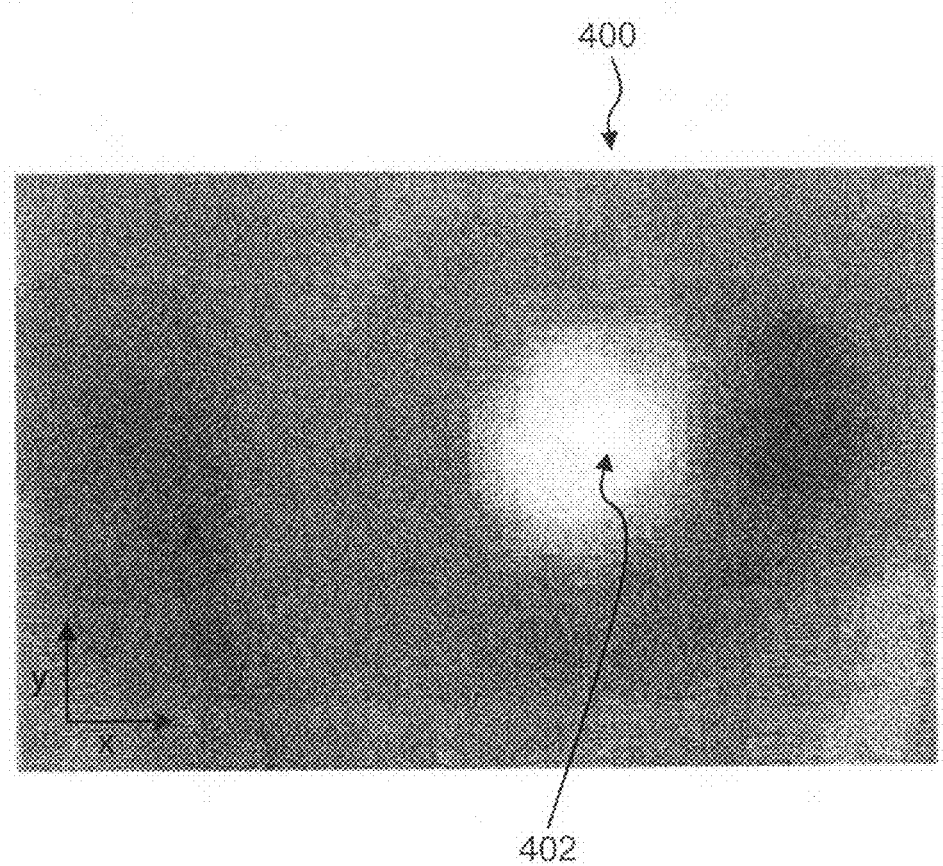
FIG. 4 shows a brightness image of the filter responses of an image of the patient eye for ring filters.

As a brightness image 400, FIG. 4 shows the value of the filter responses A, which are computed in the computer unit 118, to an image of the patient eye detected by the video camera 108. The ring filters are the basis of the filter responses and their radii (r) correspond approximately to the radius of the limbus and these ring filters have a center lying at a location (x, y) in the image of the patient eye. The darker an image point (x, y) is in the brightness image 400, the lower is the value for the filter response of the ring filter at this location. The greater the brightness of the image point in the brightness image, the greater the filter response is at this location.

The filter responses of the ring filters, which have the same radius (r) but different centers, have a maximum M in the region 402 of the brightness image 400. A ring filter is the basis for this maximum M and the center of the ring filter corresponds to the center of the limbus. The magnitude of the value of the filter response A for the maximum M is dependent upon the radius (r) of the ring filters.

Figure 5:
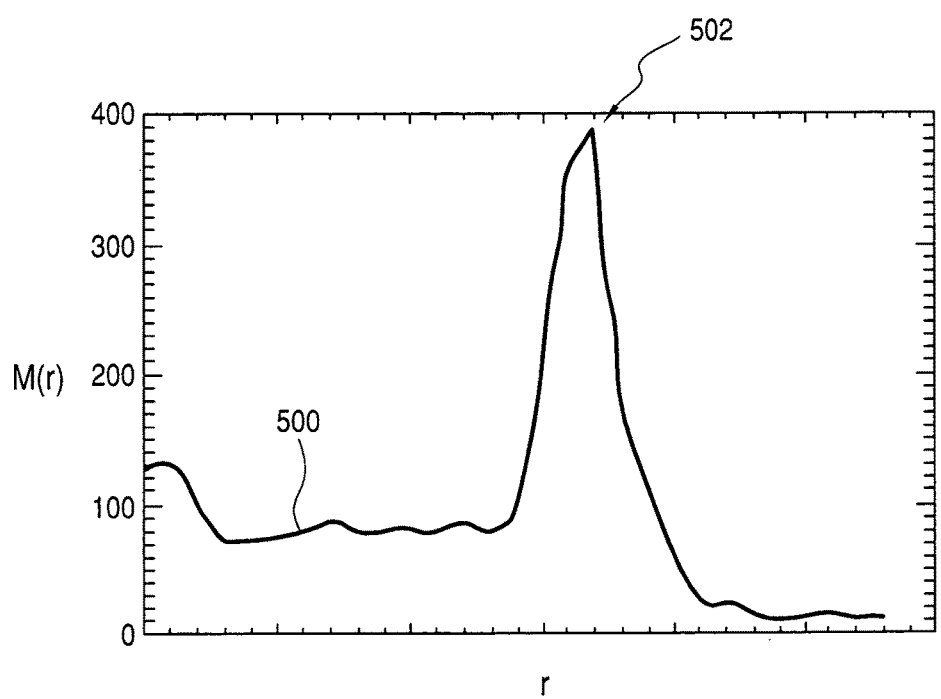
FIG. 5 shows an example of the course of the maximums of filter responses as a function of the radius of the ring filters.

With the curve 500, FIG. 5 shows a typical course of the magnitude of the maximum M(r) of the filter response for ring filters which have a different radius (r). The filter response is computed in the computer unit 118 to an image of the patient eye detected by the video camera 108.

For a ring filter for which the radius and the center correspond to the radius and the center of the limbus, the curve 500 has a maximum 502. A ring filter is the basis for the maximum 502 with the ring filter having a center corresponding to the center of the limbus and having a radius (r) which is virtually identical to the radius of the limbus.

Figure 6:
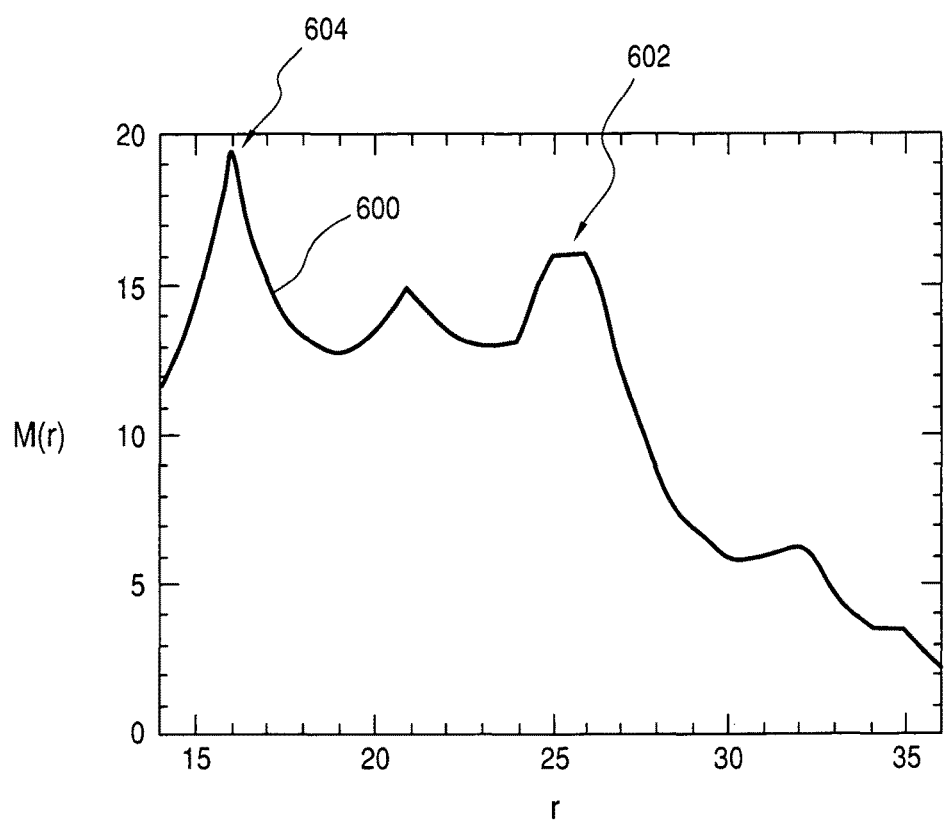
FIG. 6 shows a further example of the course of the maximums of filter responses as a function of the radius of ring filters.

The course of the magnitude of the maximum M(r) of the filter response A for ring filters having different radii (r), which each have a center in the particular image point, can, however, have a typical course corresponding to the curve 600 shown in FIG. 6. The filter response A is computed in the computer unit 118 for each image point of the image of the patient eye detected by the video camera 108. Here, the magnitude of the maximum M of the filter response A has several maxima for different radii of the ring filters, namely, a maximum 602 and a maximum 604. If needed, still further maxima can occur between one such first and second maxima.

Investigations have shown that the course of the curve 500 in FIG. 5 and curve 600 in FIG. 6 are dependent from the brightness of the pupil of a patient eye and on the characteristic coloring of the iris of the eye. In the context of the invention, it was recognized that the first pronounced maximum for the filter response A, for example, the maximum 602 in FIG. 6, is based on a ring filter which has a radius which corresponds to the radius of the limbus. The maximum for the filter response A has the largest radius. A second pronounced maximum for the filter response A, for example, the maximum 604 in FIG. 6, can result for ring filters which have a radius corresponding to the radius of the pupil of the patient eye.

In order to determine the position of a patient eye during a cataract surgical procedure by means of the visualization system 100 shown in FIG. 1, a radius for ring filters is first determined with the procedure to be described hereinafter. This radius corresponds to the radius of the limbus of the patient eye.

One such ring filter has a radius which is adapted to the radius of the limbus of the patient eye. The ring filter can then be placed with its two ring-shaped components over the limbus of the patient eye. If the center of the ring filter corresponds to the center of the limbus, the inner filter ring of the ring filter lies within the circular structure of the limbus of the patient eye. The outer filter ring is disposed then outside of the circular structure of the limbus of the patient eye.

When the radius of the limbus of the patient eye is determined, then the position of the limbus can be determined in that the image of the patient eye is correlated with the ring filters as ring-shaped comparison objects by computation of the filter response. The ring filters have a radius corresponding to the radius of the limbus and the image of the patient eye is detected with the video camera 108.

In order to track the center of the limbus in sequentially detected images of the patient eye, the filter response is computed by means of convolution in the computer unit 118 for a plurality of ring filters placed over the image of the patient eye and these ring filters have a radius corresponding to the radius of the limbus but have different centers. For the filter response of the ring filters, there results a value distribution over the image of the patient eye corresponding to FIG. 4 and this value distribution is shown in the form of a brightness distribution 700 in FIG. 7.

Figure 7:
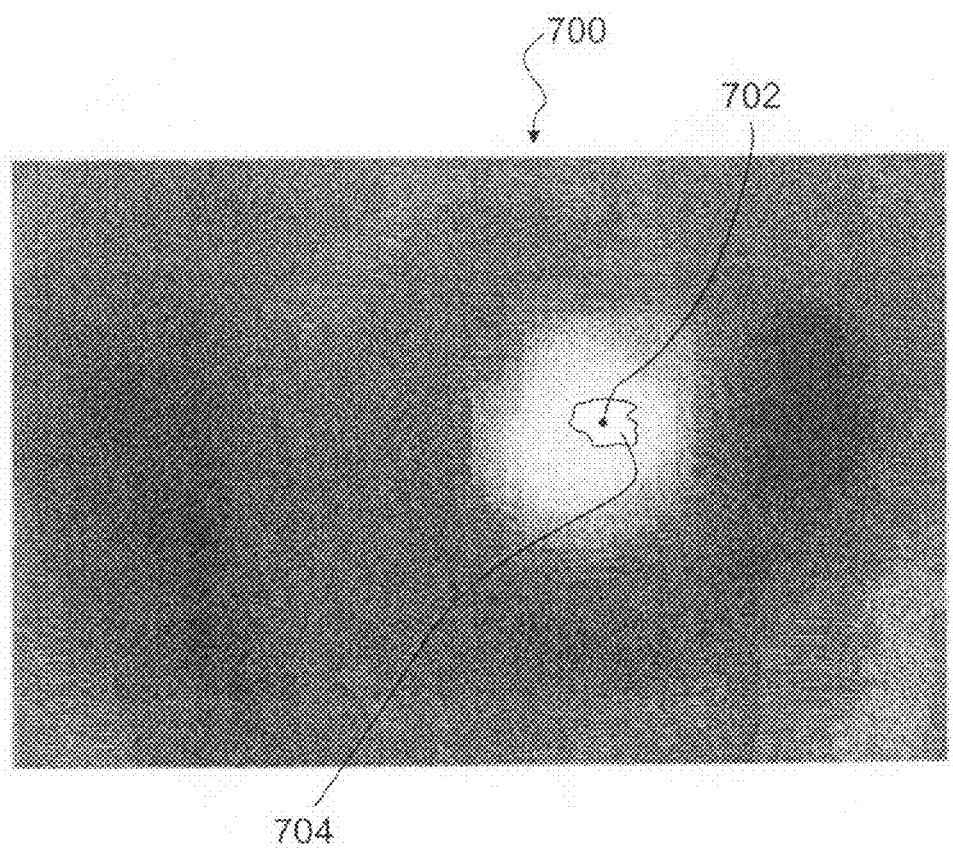
FIG. 7 shows a brightness image of the filter responses of an image of the patient eye for ring filters.
Figure 8:
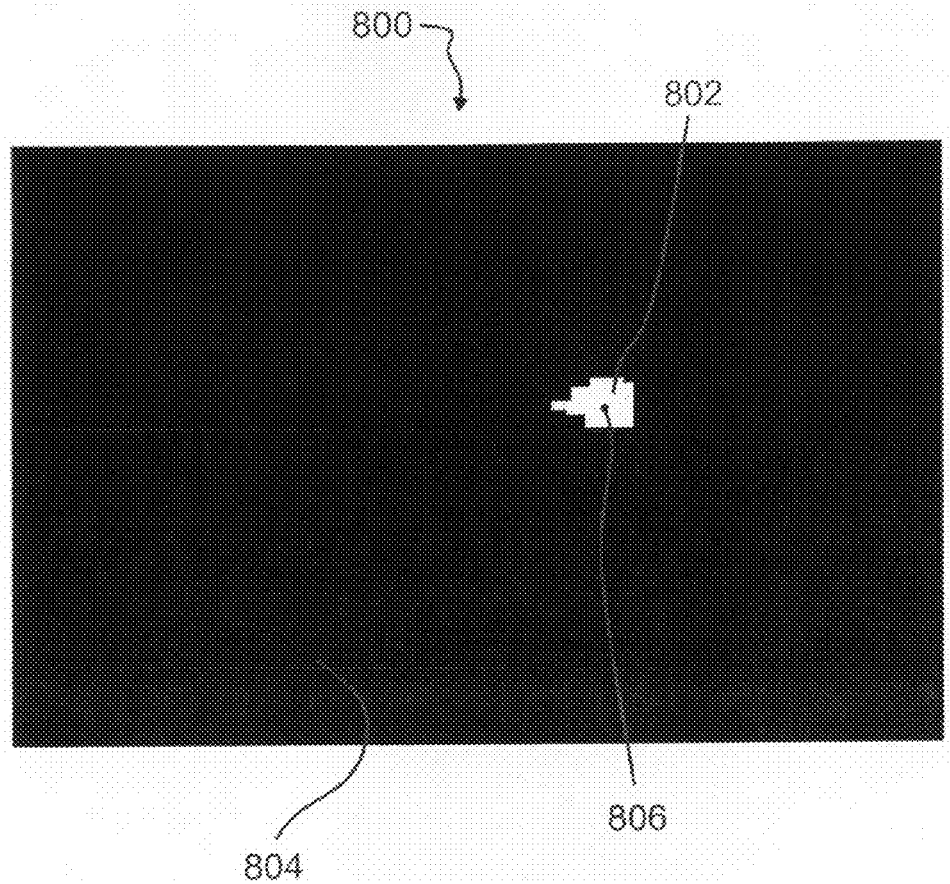
FIG. 8 shows a binary image after the formation of a threshold value for filter responses.

The filter response is a maximum for those ring filters which have a center identical to the center 702 of the limbus of the patient eye. At this location, whereat the radius of the ring filter corresponds to the radius of the limbus and the center of the ring filter corresponds to the center of the limbus, there results the maximum filter response. The center of the ring filter having the maximum filter response lies in the bright region 704 of the brightness distribution 700. In order to determine the center of the limbus from the values of the filter response for the ring filters, the values of the filter responses, which are shown in FIG. 7 as brightness distribution, are converted via threshold value formation into a binary image 800 as shown in FIG. 8.

The bright image points 802 in the binary image 800 correspond to the location of the center of ring filters whose filter response is at least 90% of the value of the maximum filter response for all ring filters. The dark image points 804 in the binary image 800 are based on ring filters whose filter response lies below 90% of the value of the maximum filter response of the ring filters.

An absolute threshold value formation is necessary in conventional edge detection methods and the problem associated with the conventional methods of selecting a suitable threshold value is not present here. This is an advantage. Each absolute threshold value formation or binarization of the image points, which are the basis of the image of the patient eye, falsifies the image. This can destroy the ring-shaped character of the limbus or the edge of the pupil.

The center of the limbus in the image of the patient eye is determined as the centroid 806 of the image points 802 in the binary image 800 after the threshold value formation for the filter responses and their conversion into the binary image.

For an image of the patient eye detected by the video camera 108, the centroid 806 is transferred in the visualization system 100 to the pattern generation unit 116.

The ring filters have a radius which was determined by means of the video camera 108 as described above. By using the ring filters, the computer unit 118 determines the center of the limbus in real time from continuous sequentially detected images of the patient eye. From this, the position of the limbus of the patient eye is displayed in real time utilizing the pattern generation unit 116 in the visualization system 100. The center of the limbus is so tracked with the visualization system 100.

Figure 9:
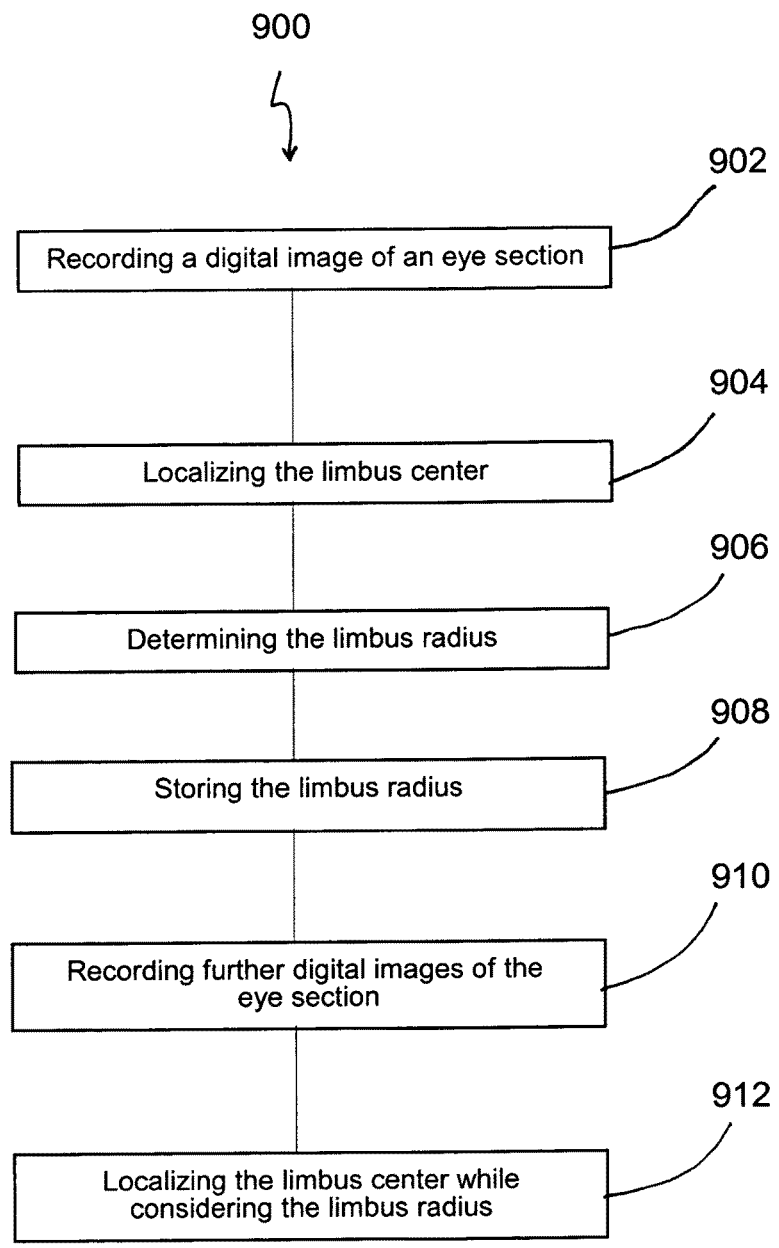
FIG. 9 shows a sequence diagram for the determination of radius and of the center of the limbus of a patient eye.

FIG. 9 shows a sequence diagram 900 for the above-described method for the determination of the radius and the center of the limbus of a patient eye with the opthalmologic visualization system 100 shown in FIG. 1.

In step 902, the image of the patient eye 102 is detected with the video camera 108. In a next step 904, the filter response of a plurality of ring filters is computed by means of convolution for the image of the patient eye. These ring filters have a radius which corresponds approximately to the radius of the limbus. The center of the limbus is localized by determining the maximum of the filter responses computed for these ring filters. In a next step 906, the radii of those ring filters are varied whose centers correspond to the center of the limbus. The radius of the limbus is then determined from the maximum of the filter response for these ring filters. In step 908, the determined radius of the limbus is stored in the computer unit 118. In a step 910, sequential images of the patient eye are detected by means of the video camera 108 in the visualization system 100. In step 912, these images are convoluted with ring filters which have the radius stored in the computer unit 118 in step 908. From the maximum of the computed filter responses, a conclusion is drawn as to the position of the limbus of the patient eye in the computer unit.

Figure 10:
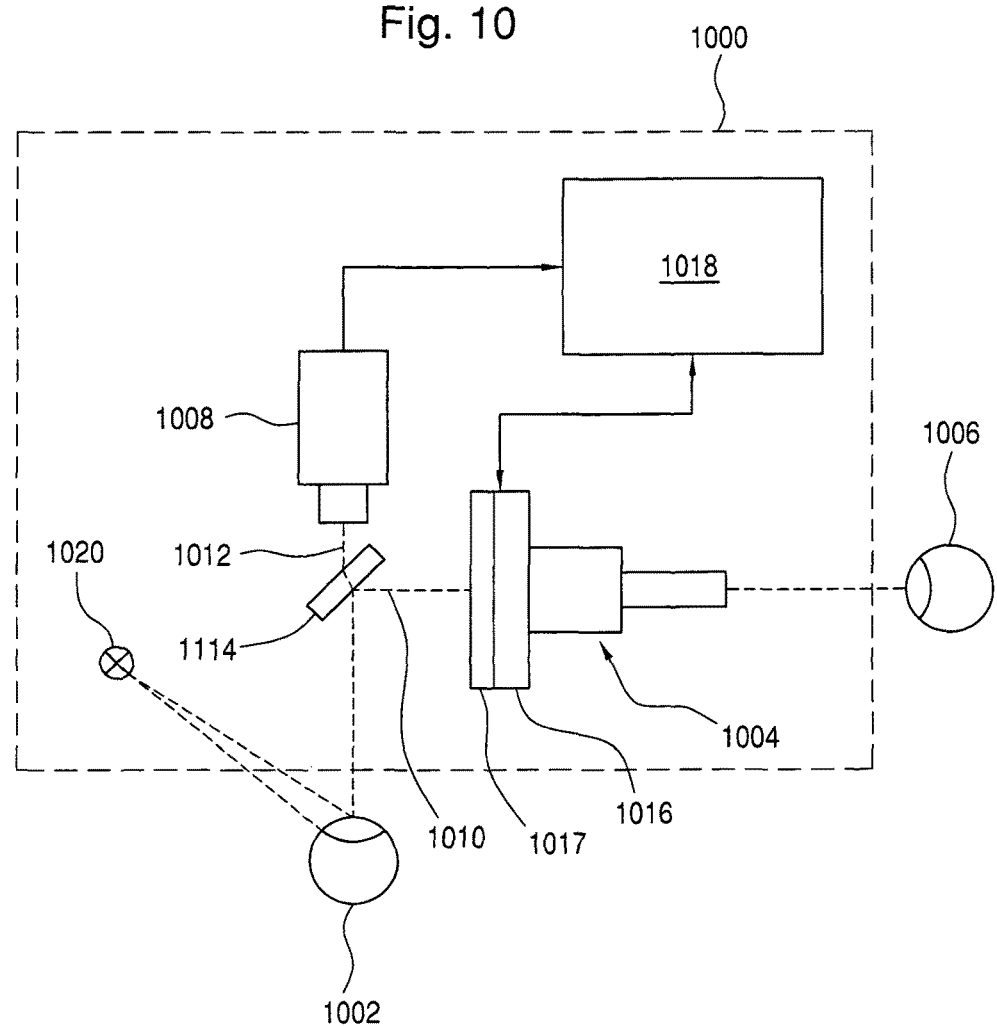
FIG. 10 shows a further opthalmologic visualization system.

FIG. 10 shows an opthalmologic visualization system 1000 which has a light source 1020. The patient eye 1002 can be illuminated with white light by means of the light source 1020. Insofar as the visualization system 1000 has component groups which correspond to the component groups of the visualization system 100 of FIG. 1, they are provided with the same reference numerals as in FIG. 1 increased by 900.

The visualization system 1000 includes an eye viewing system 1004. The eye viewing system 1004 visualizes the patient eye 1002 for a viewer having a viewing eye 1006 in an ocular. The eye viewing system includes a pattern generation unit 1016 having an LCD-display 1017. With the LCD-display 1017, display information, which is generated by the pattern generation unit 1016, can be superposed onto the image of the patient eye 1002 for a viewer in the ocular of the eye viewing system 1004. The visualization system 1000 includes a video camera 1008 which is configured as a color camera. The video camera 1008 has a red (r), a green (g) and a blue (b) color channel. The video camera 1008 generates images of the patient eye 1002 which contain the information of the red, green and blue color channels.

Investigations in the context of the invention have shown that the center and the radius of the limbus of an image of the patient eye, which is detected by the video camera, can be detected especially accurately and reliably also during surgery in that the red color channel of the video camera 1008 is applied for a comparison of the image of the patient eye 1002 to ring-shaped comparison objects as described above.

Figure 11:
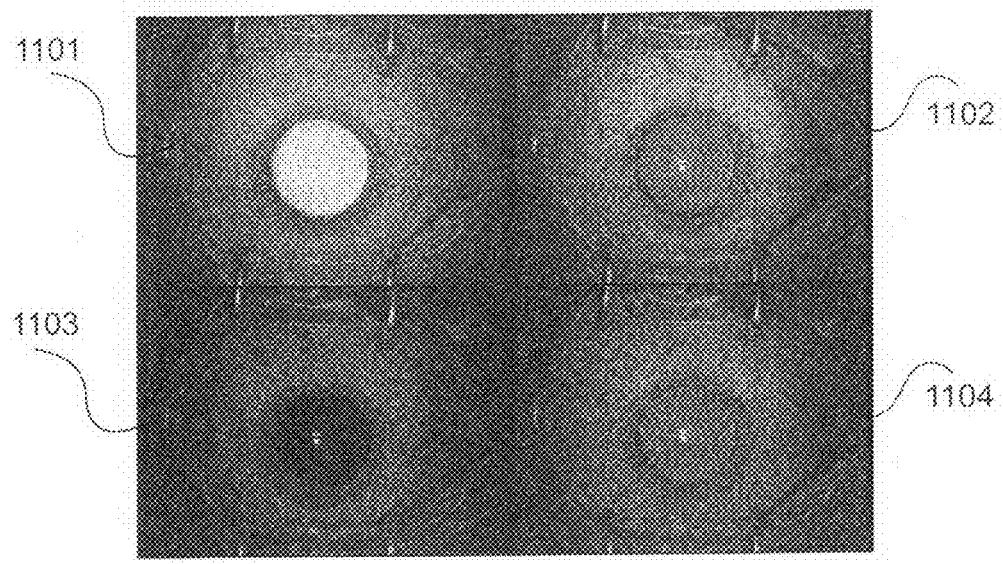
FIG. 11 shows images of the patient eye in advance of a surgical procedure.

FIG. 11 shows corresponding images 1101 to 1104 of a patient eye in advance of a surgical procedure. The image 1101 is a red component of the image of the patient eye detected by the video camera 1008. That is, the signal of the red color channel of the video camera 1008 is the basis of the image 1101. The image 1102 corresponds to the signal of the green color channel of the video camera 1008. The image 1103 is based on the signal of the blue color channel of the video camera. The luminescence signal of the video camera 1008 is the basis of the image 1104. The luminescence signal corresponds to the sum of the signals of the red color channel, the green color channel and the blue color channel of the video camera 1008. The image 1103 of the patient eye is based on the blue color channel of the video camera. In this image 1103 of the patient eye, the limbus can be seen with very good contrast.

The image 1103 shows the patient eye with a sclera with many vessels running therethrough. The blue color channel therefore visualizes especially the blood vessels of the patient eye. In the image 1104 of the patient eye, the structure of the blood vessels is also more dominant than the structure of the sclera and the limbus.

The red color channel of the video camera 1008 is the basis of the image 1101. The image 1101 has less contrast compared to the image 1103. However, no edge structures are encountered in the image except for the clear transition in the region of the limbus. These edge structures could disturb the determination of the center and radius of the limbus via correlation with the ring-shaped comparison objects.

Figure 12:
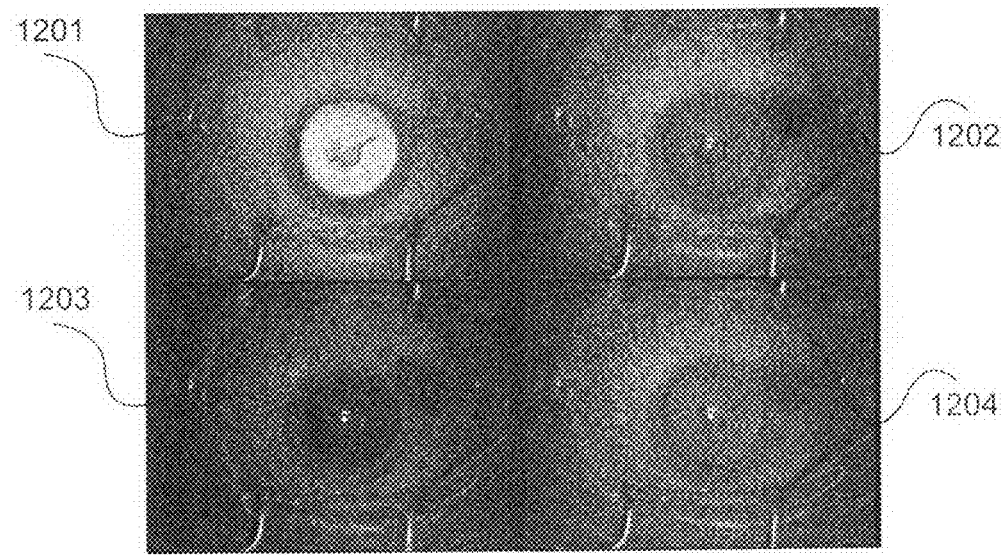
FIG. 12 shows images of a patient eye after a surgical procedure.

FIG. 12 shows images 1201 to 1204 of a patient eye which is subjected to a surgical procedure. The image 1201 is a red color component of the image of the patient eye detected by means of the video camera 1008. The signal of the red color channel of the video camera 1008 forms the basis of this image. The image 1202 corresponds to the signal of the green color channel of the video camera 1008. The image 1203 is based on the signal of the blue color channel. The image of the patient eye, which corresponds to the green, blue and luminescence signals, is so modified by hemorrhages in comparison to corresponding presurgery images that the image has elements which have an intense contrast to the sclera. These image components in the image 1203 make localization of the limbus considerably more difficult. In the image 1203 based on the blue channel of the video camera 1008, the structure originating from a hemorrhage is even so dominant that one can hardly locate the pupil edge. Only in the image 1201, which is based on the red color channel of the video camera, is the structure of the sclera not affected by hemorrhages.

Figure 13:
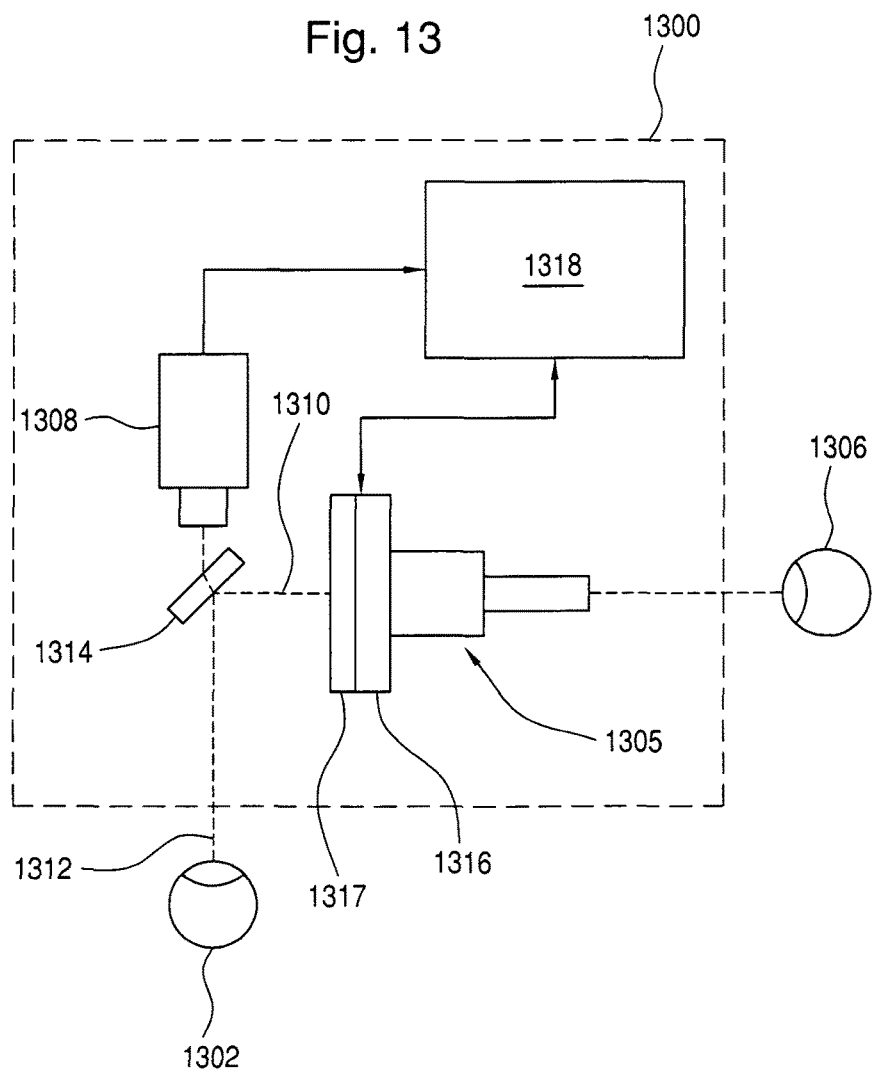
FIG. 13 shows a further opthalmologic visualization system.

FIG. 13 shows an opthalmologic visualization system 1300. The visualization system 1300 includes a surgical microscope 1305. The surgical microscope 1305 is an eye illuminating system for the patient eye. The surgical microscope has an imaging optic having an ocular. There is a video camera 1308 in the visualization system. The video camera has an imaging beam path 1312 for detecting images of a patient eye 1302. A viewing person having a viewing eye 1306 can view the patient eye 1302 with an imaging beam path 1310. A beam splitter 1314 is provided in the visualization system 1300 for superposing the imaging beam paths of the surgical microscope 1305 and of the video camera 1308.

The visualization system 1300 contains a computer unit 1318 and a pattern generation unit 1316. An LCD-display 1317 is assigned to the pattern generation unit 1316. The pattern generation unit 1316 is connected to the computer unit 1318. Auxiliary patterns can be generated by means of the LCD-display 1317 assigned to the pattern generation unit 1316. These ancillary patterns are superposed onto the image of the patient eye 1302 in the surgical microscope 1305.

The computer unit 1318 determines the radius and the position of the center of the limbus of the image of the patient eye 1302 in the same manner as the computer unit 118 in FIG. 1 and the computer unit 1018 in FIG. 10. The computer unit 1318 determines this radius and position in that, as described above, ring-shaped comparison objects, which are configured as ring filters, are correlated with the image of the patient eye. In addition, the computer unit 1318 computes a quantity Z for the reliability of the position of the center of the limbus and of the radius of the limbus of the patient eye 1302. This position of the center of the limbus and the radius of the limbus is determined via the correlation of the ring-shaped comparison objects with the image of the patient eye 1302 detected by the video camera 1308.

For this purpose, the computer unit 1318 compares the filter response $A_{image}$ of that ring-shaped comparison object whose center corresponds to the center of the limbus and whose radius corresponds to the radius of the limbus and whose amount $\text{Max}(|A_{image}|)$ is therefore at least local maximum as described above, to the value of the maximum amount $\text{Max}(|A_{referenceimage}|)$ of the filter response $A_{referenceimage}$ of a ring-shaped comparison object for a reference image.

The computer unit 1318 utilizes the following formula:

$$Z := \text{Max}(|A_{image}|)/\text{Max}(|A_{referenceimage}|)$$

In accordance with this formula, the following applies for the values Z of:

$$0 \leq Z$$

The reference image can be especially an artificially generated image. It has then preferably a structure corresponding to the ring-shaped comparison object applied for the comparison to the image of the patient eye. This structure is present in a dark disc on a bright background with the dark disc corresponding to the ring-shaped comparison object. In this case, Z can assume the following values:

$$0 \leq Z \leq 1$$

The larger Z is, the better does the center and the radius of the particular ring-shaped comparison object, for which the filter response is maximal to the image of the patient eye, match to the actual radius and center of the limbus in the image of the patient eye.

In the visualization system 1300 and by means of the pattern generation unit 1316, the quantity Z for the reliability of the position of the center of the limbus and of the radius of the limbus of the patient eye 1302 is also displayed to the viewing person in the surgical microscope 1305. This position is determined via the correlation of ring-shaped comparison objects with the image of the patient eye 1302 detected by the video camera 1308. The display for the quantity Z takes place in the form of a variation of a pattern ring displaying the position of the limbus of the patient eye and by a display bar in the image of the surgical microscope 1305 and generated by means of the pattern generation unit 1316.

In visualization system 1300, the pattern ring, which displays the position of the limbus of the patient eye in the surgical microscope 1305, has a solid line when the quantity Z lies above a threshold value. The pattern ring is shown by a broken line when the quantity Z drops below the threshold value. The absolute magnitude of Z is visualized by means of the length of a display bar.

During the course of a surgical procedure, a surgeon can obtain the information as to whether the radius and position of the limbus of the patient eye are correctly determined with the system.

Figure 14:
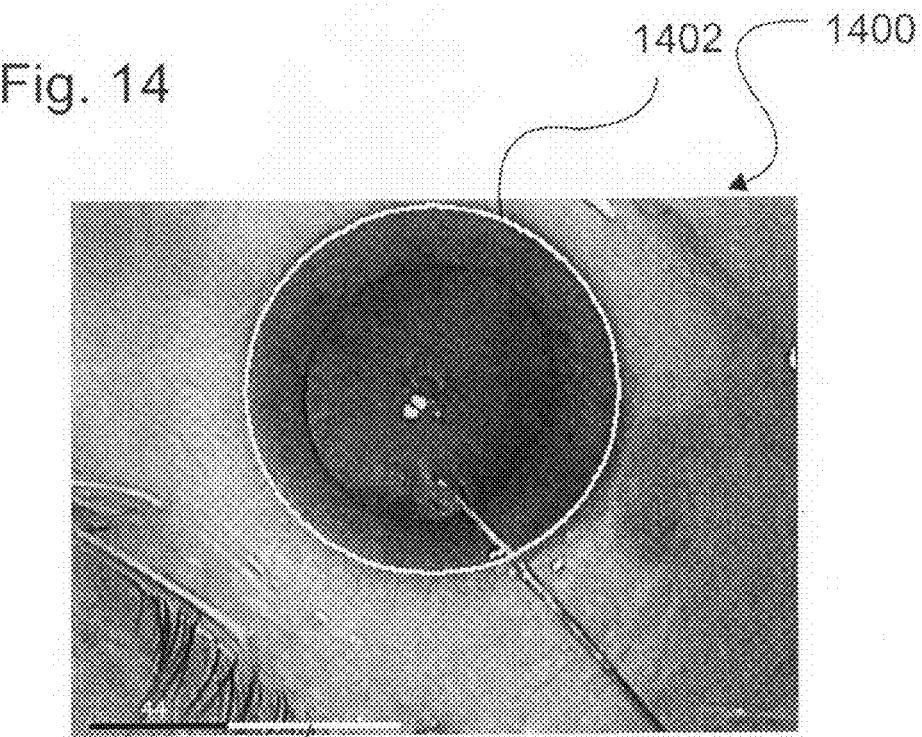
FIG. 14 shows an image of the patient eye detected with the visualization system; and, FIG. 15 shows a further image of the patient eye detected with the visualization system.

FIG. 14 shows the image 1400 of a patient eye 1302 with a surgical instrument 1401 for a viewing person in the surgical microscope 1305 of the visualization system 1300 of FIG. 13. A pattern ring 1402 is generated by means of the pattern generation unit 1316 in the visualization system 1300. In the image, which is visualized by the surgical microscope 1305, the pattern ring 1402 is superposed positionally correctly on the image of the patient eye 1302. The center of the pattern ring 1402 corresponds to the center of the limbus in the image 1400 of the patient eye. The pattern ring 1402 has a radius which corresponds to the radius of the limbus of the patient eye 1302.

The pattern ring 1402 is an aid for the surgeon during cataract surgery. With the pattern ring 1402, a suitable position for the incision in the cornea of the patient eye 1302 can be displayed to the surgeon with this incision being needed for the cataract surgery.

The quantity Z is visualized by means of a display bar 1404. Basically, the quantity Z can, however, also be displayed in the form of numbers, for example, as a percentage amount or as a bar diagram.

Figure 15:
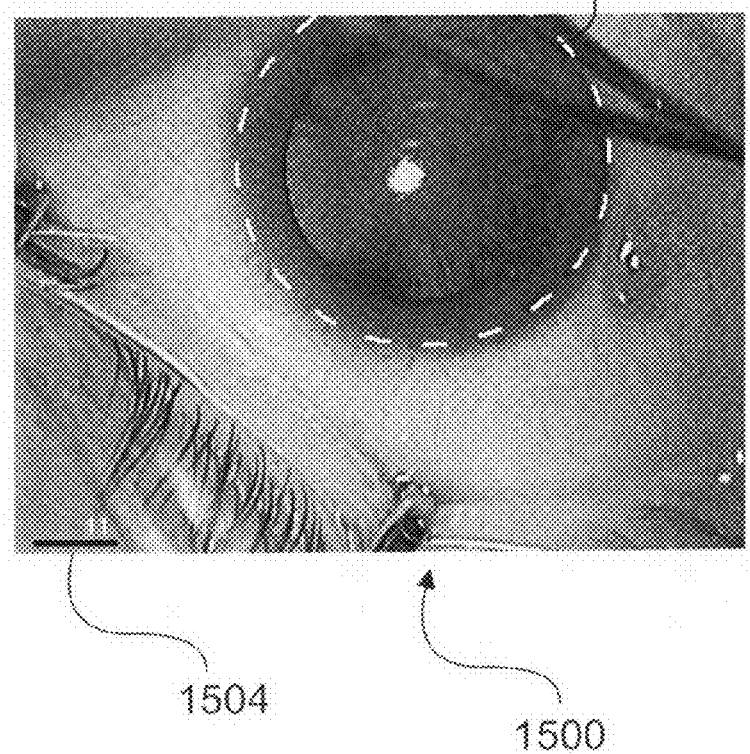

In FIG. 15, an image 1500 of a patient eye 1302 is shown in the surgical microscope 1305 of the visualization system 1300 of FIG. 13. Here, the quantity Z is less than for the image 1400 of the patient eye 1302 in FIG. 14. The display bar 1504, which visualizes the quantity Z, is here therefore shorter than in FIG. 14. The pattern ring 1502, which visualizes the position of the limbus of the patient eye, has a broken line because of the lower value of Z.

Basically, it is possible that the quantity Z in the viewing image of the surgical microscope 1305 can be displayed in the visualization system 1300 in another manner.

With respect to the foregoing, the following is added:

It is especially advantageous when the display unit for the reliability of the aid information is configured as an optical imaging unit. It is of special advantage to show the corresponding information as to the reliability in the viewing field of the surgical microscope to the surgeon. The information can, for example, be projected in or directly next to the eye being treated. This information can, however, also be faded into the imaging beam path of the surgical microscope.

The described opthalmologic visualization systems make possible not only the determination of the position of the characteristic components of a patient eye but also the tracking of the position thereof with a method which is robust with respect to disturbing influences and which operates rapidly and reliably independently of the individual configuration of the eye.

Based on the correlation of the digital image recording to be analyzed, a ring-shaped bright-dark transition is determined in the digital image recording with a ring-shaped comparison object having a fixed radius. The size of the comparison object is predefined and is not dependent upon the image content and the bright-dark transition corresponds to the comparison object. The comparison object is predefined independently of the image content of the instantaneous image and is preferably stored. The correlation takes place while the location varies so that the correlation function is a function of the location variables. The values of the image points of the image are computed with the values of the image points of the comparison object while the comparison object is moved over the image. That is, the center of the comparison object comes to lie on each image point of the image. Accordingly, for each position of the comparison object, a value and therefore a quantity for the coincidence of the image and the comparison object results. When the comparison object and a feature, which corresponds to the comparison object, are coincident in the image recording, the measure for the coincidence of image recording and comparison object is the largest.

The points of the image $I(x,y)$ and the comparison objects as well as the result of the correlation of comparison object with the image, for example, the result of the correlation in the form of filter responses $A(x,y)$ together form three two-dimensional fields of image points. The comparison objects can be filters.

In the correlation, the comparison object, for example, a filter, is pushed over the image and for each position $(x0, y0)$ of the center of the comparison object or of the filter, the result $R(x0,y0)$ is computed. Preferably, the comparison object or the filter is not displayed beyond the image edge.

For correlation in the form of convolution with a filter, the value of each point of the filter is multiplied by the value of an image point of the image which lies under the point of the filter. The results of all of these multiplications are then added. The correlation can also take place by a template comparison. For this purpose, the values of all those image points are added which correspond to the image points of the template.

When a rapid position determination is wanted, the position of the comparison object, for which a maximum value of the coincidence results, is selected as a position of the characteristic eye component. It is also favorable to select a position whose value of the coincidence does not deviate by more than 20%, preferably less than 10%, ideally less than 5%, from the maximum of the coincidence. It is possible to access additional criteria such as the color of the characteristic eye component or the slope of the brightness increase in order to realize a determination of a characteristic eye component with this determination being based on additional features.

The radius of the comparison object is determined preferably in an initialization step wherein the image detail to be analyzed is correlated in each case with ring-shaped comparison objects of different radii. In the correlation of the image detail with comparison objects of different size, the coincidence is determined which is best for the comparison object and, based on the comparison of the values of the best coincidence, the above all best coincidence and therewith the comparison object with the size is determined which is best adapted to the object under investigation. This takes place in an advantageous manner in that the particular maximum response of the correlation function is plotted for the comparison object as a function of its radius. The correlation function results from the correlation with the image detail. A function results which always forms a maximum when the radius fits well to the radius of a corresponding object in the image detail under investigation. The maximum which results for the largest radius belonging to a maximum value corresponds to the radius of the largest ring-shaped object in the image detail and therewith the limbus radius which was recognized in the course of the method. This radius so determined is selected as a fixed radius for a comparison object which is suitable to follow the limbus and therewith also the limbus center during the eye investigation or during treatment, that is, with the evaluation of subsequent recordings of the same object. This initialization step requires a clearly larger amount of computation and therefore a greater time factor than the subsequent tracking or following of the already known object with a comparison object of defined size. Since this takes place only at the start of the examination or treatment, it is acceptable.

During the examination or treatment, a detection of the limbus center has to take place, facilitated by maintaining the radius of the comparison object in real time. Since the chances of hitting the target are significantly higher when utilizing the radius for the comparison object, which was initially determined to be precisely fitting, than when using an arbitrarily selected radius, it is in any event justified to accept this larger time span for the determination of the radius. What is important, however, is that the determination does not take place for each recording, rather, that after the initially completed determination of the fitting radius of the comparison object, it can always be used again thereafter.

Preferably, the ring-shaped object is built up from two concentrically arranged ring-shaped components. Because the comparison object has at least two components, the possibility results to adapt a first component to the eye region outside of the brightness transition (for example, the sclera) and a second component to the eye region, which lies within the brightness transition (for example, the iris). With these two components, the brightness transition can be intensified to a certain extent via the correlation with the comparison object. The optimal coincidence with the comparison object results when the inner ring of the comparison object lies, for example, on the iris and the outer ring lies, for example, on the sclera. The transition region, here the limbus edge, is enclosed by the two ring-shaped components. The limbus center comes into coincidence with the center of the comparison object. With this configuration of the comparison object, not only the form feature (that is, the ring-shaped or circularly-shaped appearance of the limbus or of the pupil) is used for searching for the transition object but also the area feature (the brightness transition).

Preferably, the two components of the comparison object are two narrow ring-shaped components which are so far spaced from each other that none of the components comes to rest in the transition region of the brightness increase. Instead, one comes to rest in a region of low brightness and the other comes to rest in a region of high brightness. In this way, a clear identification of the object is possible. If the limbus radius is not determined initially, then the distance of the two ring-shaped components is preferably to be selected such that the outer ring lies reliably outside the edge of the transition object and the inner ring lies reliably within the edge of the transition object, that is, of the limbus or of the pupil edge.

In this embodiment, a suitable distance can be found empirically based on the examination of a larger number of typical recordings of a patient eye with the video camera in an opthalmologic visualization system. In the context of the invention, it has been shown that, for a resolution of the recording of at least 100×100 pixels, which makes it possible to determine the center of the limbus with an accuracy of at least 1 mm, which is required for a surgical procedure, a distance of the inner ring from the outer ring between one and five pixels of the image sensor of the video camera, preferably a distance of two pixels, is very suitable.

In the context of the invention, the correlation of the comparison object with the recording can take place also in the form of a difference formation of the ring-shaped components of the comparison object, that is, the regions, which are correlated with the comparison object within the recorded eye detail. Accordingly, preferably, with the correlation, the one ring-shaped component of the comparison object is provided with a positive sign and the other is provided with a negative sign. The comparison object is preferably so configured, that is, the Correlation function so selected that, in a correlation with a gray surface, that is, a surface without a defined brightness transition, a neutral result is obtained, for example, the value zero. Only for a defined brightness transition on which the comparison object comes to rest, does an increased value of the correlation function result.

A comparison object can also be realized by a filter with which the image of the patient eye is convoluted. This filter is ring-shaped and is so configured that a maximum filter response always results when the ring-shaped filter comes to rest on a ring-shaped brightness transition such as the limbus or pupil edge. This maximum of the filter response is much more clearly defined the better the coincidence of the filter radius is to the radius of the sought-after object. For this reason, and preferably in correspondence to the above-explained method, the radius of the filter is determined in an initialization step before the tracking of the eye takes place with a fixed filter radius. The eye tracking accompanies the examination or treatment. As a preferred ring-shaped filter, a filter is selected which has two concentrically arranged components so that a maximum filter response can be obtained when the one component comes to rest completely in the region of low brightness and the other component comes to rest completely in the region of higher brightness and accordingly, the transition region, which is to be identified (such as, for example, the limbus) is completely enclosed by the two components. The distance of the two ring-shaped components is selected to be so large that no component lies in the transition region and instead, both clearly lie in one brightness region and simultaneously the distance is selected so small that a radius determination as exact as possible is possible.

In order to not always have to carry out this initialization step when there is a change of the object radius because of changes of the recording conditions (such as microscope magnification factor), in a preferred embodiment, each change of the apparatus settings is included in the computation of the size of the ring-shaped comparison object or the filter radius is correspondingly adapted. These apparatus changes act on the size of the recorded eye detail. In this way, it is ensured that the radius of the comparison object is automatically adapted to the recording conditions and need only be determined once initially. For this purpose, it is necessary to provide an interface between the apparatus, which changes the apparatus parameter, for example, the microscope, and the unit where the correlation with the comparison object takes place.

Even though the ring-shaped configuration of the comparison object is important, it would not make a significant difference with respect to the method if a polygon or the like would be used. It is also not necessary that a closed ring be used. The comparison object can also be put together from ring-shaped segments. What is essential for the method is only that, in total, the ring-shaped character of the comparison object is retained. Indeed, and especially in the edge region of the image, it is even more reliable to use only ring segments. With these ring segments, preferably that region is omitted which lies at the edge which the comparison object approaches during correlation and therefore also the limbus in the image. In this way, the comparison object during correlation better corresponds to the object to be found which is partially cropped as soon as it lands at the peripheral region of the image.

It is advantageous when the red color component is always used for the correlation with the comparison object. It has surprisingly been shown that this is the least affected by disturbances during the eye treatment because in this color component, the red of the hemorrhages and small vessels forms a homogeneous surface with the white of the sclera. In this way, a more reliable result can be obtained in this color channel than in other color components. Because the red channel is always used as a gray scale image, a high accuracy can be achieved and the method is accelerated compared to the use of a multicolor image or the continuous selection of the color channel actually in richest contrast.

In order to optimize the method, it is advantageous to reduce this gray scale image to the extent which the required accuracy permits. This step can be omitted for a correspondingly high computing capacity. Furthermore, it is advantageous to homogenize the image in order to eliminate small unimportant contrast transitions which would adulterate the result.

Especially when the localization is to take place over the entire examination or treatment as eye tracking, it is of fundamental significance for the localization method, which is to be used, that the method operates extremely rapidly so that the assist, which is derived from the determined position or characteristic, is always immediately faded into the eye to be treated or is displayed in some other way. The derivation of the position and/or characteristic and the indication of the assist therefore has to take place if possible without a time delay.

This is often difficult especially in the detection or tracking of the limbus because the contrast between the limbus and the white sclera is not all too large with some iris colors and is not always pronounced compared to the contrast between blood vessels and the white of the sclera. Especially in cataract surgery, during which large blood spots can appear on the sclera during the surgery and whose contrast to the white of the sclera is often greater than the contrast between the limbus and the sclera, a rapid reliable detection of the limbus can be difficult.

With the use of only one color component of the multicolored image, preferably a gray scale representation of the digital image, the set of data which is to be analyzed can be greatly reduced and therefore the method can be considerably accelerated. The gray scale representation is derived from the red channel of the recording video camera. The best suited color component must be used in order to optimize the reliability of the method. This color component should be used preferably during the entire method and must therefore be suitable for all images. It would be, in principle, possible to determine the suitable color component anew for each start of the corresponding method. This, however, would greatly slow the method and would no longer permit a real time analysis. The color component which is best suited for the evaluation by means of image processing is, in principle, that color component wherein the contrast between the characteristic eye component, which is sought, and its surroundings is the highest. To decide which color component is the one for the particular eye to be treated can be very complicated when it should apply to all eyes because large differences between the eyes per se exist, especially, however, between diseased eyes. In some eyes, the iris is extremely bright and the pupil very dark (almost black). Another time, the pupil is bright or milky because of a cataract and the iris can be dark brown, almost black. There are cases wherein the iris and pupil are virtually the same with respect to their color and, for this reason, it is always relatively difficult in these recordings to separate iris and pupil. Especially for diseased eyes, the sclera can be colored and when the iris is relatively bright, little contrast to the iris is provided. Furthermore, the sclera is also permeated by disturbing blood vessels and can be affected by hemorrhages and instruments introduced during the treatment which, for a method, which is to be used during the entire treatment, likewise has to be considered. It is difficult to define a color component which permits an identification of position and properties of characteristic eye components and which is permissible for all eye types and especially also in the course of all treatments. Surprisingly, it has, however, been shown that the red color component is virtually always that color component which is affected the least by disturbances even during the eye treatments because, in this color component, the red of the hemorrhages and vessels form a homogeneous surface with the white of the sclera.

Even though the red color component is often not the most contrast rich color component, it has been shown that its resistance relative to disturbances, which are caused by blood, is of such a great significance that it supplies the most reliable results. Especially advantageous is the use of a red color component of the digital image when, as a characteristic eye component, the limbus is localized, that is, the transition between the sclera and the iris. Even though it often does not show the transition having the most contrast, this is a very reliable magnitude to be identified especially in this color component because the iris, in general, always distinguishes in its color from the sclera and the sclera is little affected in the red color component by the treatment. In this way, it is ensured that this transition in the red color component exhibits not extremely high but adequate contrast in order to identify the transition. If, accordingly, a method should be so fast that it does not permit a renewed selection of a suitable color component, then a combination of a localization of the limbus of the eye and the use of the red color component to identify the same is the suitable selection which always ensures an adequately reliable result. Preferably, the red channel of the camera of the eye examination or treatment apparatus is used for the derivation of the red color component which preferably lies in a wavelength range from 550 to 750 nm. Preferably, the sensitivity maximum of the recording camera for red lies in the range from 590 nm to 610 nm. In this way, one can work with the normal recording of the diagnosis or treatment apparatus such as the surgical microscope, for the localization and tracking of eye components. Only in this way is it at all possible to track the limbus during the surgical procedure on the eye. It would be impossible to switch in another illumination and switch off the usual white light illumination for localizing the limbus during surgery. This would unacceptably affect the surgery itself. Furthermore, this color region has been shown to be very advantageous because the blood vessels appear almost white therein and therewith form a unified surface with the white of the sclera.

It is especially advantageous to use this method when the characteristic eye component is not only to be identified once but is to be tracked during the entire treatment. Accordingly, the selected color component has to be the most resistant to all possible disturbances which can occur during the treatment.

The method can be advantageously realized when the characteristic eye component is realized via a correlation of the image with the ring-shaped comparison object and the red color component is the basis for the correlation. This can, for example, take place in the form of a comparison to a template or a convolution with a ring filter. With the selection of an imaging process method of this kind and the selection of a red color component for all images to be analyzed, the speed of the method can be greatly accelerated and an analysis of the images can be achieved in almost real time. An extremely rapid and reliable method results especially when the limbus is looked for via a correlation of the red color component with a ring-shaped filter.

Preferably, the ring filter is so configured that it comprises two ring-shaped components between which the difference is formed with the convolution. For this purpose, with the convolution, the one ring-shaped component of the filter can be provided with a positive sign and the other with a negative sign. Ideally, the filter or its ring-shaped components are so selected that, with convolution with a gray surface, that is, a uniform surface without brightness transition, a neutral result such as zero results whereas the filter, in a convolution with a surface in the region of the brightness transition, produces ever greater values with increasing intensity of the transition.

In a further advantageous embodiment, a red color component of the digital image is used in order to identify the edge of the characteristic eye component based on an edge detection method. Especially when this edge is coincident with the limbus, the red color component should preferably be used because the limbus, for the reasons explained above, can always reliably be identified in the red color component. Even though the threshold value determination is still critical in the edge detection method, this channel supplies a reliable basis also with such a method to make possible a relatively rapid and reliable finding of the characteristic eye component.

Preferably, a red color component is also the basis for binarizations which are undertaken in the context of such a method for determining the radius or position of characteristic eye components by means of methods for image processing. Each binarization is decisively simplified because, in the red color component, all blood vessels and hemorrhages which are caused by the treatment can be suppressed or eliminated. The binarization method can concentrate on the characteristic eye components which are actually to be localized without being excessively affected by disturbances.

According to the invention, essential characteristics, such as the radius or the position, preferably of the center of characteristic eye components, are determined during an eye examination or treatment in that, in a first image, which is recorded of an eye detail during an eye treatment or eye diagnosis, the characteristic eye components are searched for and a quantity, which characterizes the eye component, is derived. This characteristic quantity is used in order to localize the characteristic eye component more rapidly and easily anew in each further recording of the same eye in the context of the same eye examination or eye treatment. The recording is made with the same camera. The localization takes place automatically in each case with methods of image processing, preferably, with a correlation method with an edge detection method or with other known methods.

The idea on which the invention is based is to take a little more time at the start of the eye examination or eye treatment as long as it is not too critical as to time in order to derive a characteristic quantity, which characterizes the eye component, in a somewhat complex but very reliable method step. This characteristic quantity can subsequently be used during the remainder of the course of the eye examination or treatment. Thereafter, in a simplified method, this quantity is used as known quantity to very rapidly and likewise reliably derive the value of the eye component which is to be determined. Because more time is taken in a first method step and a characteristic quantity is derived, stored and used again and again, there results the possibility to create a very reliable method which is slow only with the first recording, which is to be evaluated, but works for all further recordings during the examination or treatment in almost real time and ensures therewith that, for example, assists or patterns can be faded into the image, which corresponds to the actually analyzed image, which the viewer sees in the microscope or the like, with possibly a slight delay to the image recording. Without the reuse of a characteristic quantity for the further method steps, either the time intensive method must always be carried out again in order to obtain a reliable result, or accuracy has to be dropped in favor of the rapidity of the method. Only, the split into two method steps, that is, one very precise but time intensive method step and a subsequent second, very rapid method step which is only accurate in that it relies on quantities derived in the first method step, makes it possible to realize a simultaneously very reliable but also very rapid method.

Preferably, for the localization in the first image as well as in the subsequent methods for the localization in all subsequent images, the same principle of an imaging processing method is used, that is, the localization takes place in each case with correlation, edge detection or a corresponding method which is selected. This has the advantage that only one method principle need be programmed and that the localization method and the subsequent method only differ in that, because of the consideration of the characteristic quantity in the subsequent method, in this method part, a part of the method can be jumped over. The localization method is therefore shortened and more rapid.

In an advantageous embodiment of the method, the limbus or the pupil radius is derived as a characteristic quantity so that for the subsequent method, that is, for the second and each further localization of the characteristic eye component, it is already known how large the characteristic eye component is which is looked for. This recognition is the basis of the idea that the magnitude of the characteristic object, which is looked for, is only decisively changed in the course of the method when the recording conditions change, otherwise, it remains approximately constant. An object in an image whose size is already known is found clearly easier and more rapidly than an object of which nothing is known. Especially for the recording of an eye detail wherein the circularly-shaped limbus or the circularly-shaped pupil is a very dominant component, the possibility is provided with the derivation and further use of the radius, to develop a comparatively simple method for tracking the position of the characteristic eye component, that is, the limbus or the pupil.

In a preferred embodiment, the radius of the characteristic eye component is determined in a localization method in that the image detail, which is to be analyzed, is in each case correlated with ring-shaped comparison objects having different radii. In the correlation of the image detail with the comparison objects of different size, for example, in a template method or filter method, in each case, the best coincidence for the comparison object is determined and based on the comparison of the values of best coincidence, the absolute optimal coincidence is determined and therefore, the comparison object with the quantity is determined which is adapted best to the characteristic object which is looked for. This takes place advantageously in that the particular maximum response of the correlation function which results with the correlation with the image detail is plotted for the comparison object against the radius thereof. A function results which always forms a maximum when the radius fits well to the radius of a circularly-shaped or ring-shaped characteristic eye component in the image detail.

The maximum which results for the largest radius corresponding to the maximum value corresponds to the radius of the largest ring-shaped object in the image detail and therewith to the limbus radius. The determination of the radius based on the correlation with ring-shaped comparison objects of different size has been established as a method which is superior to conventional edge detection methods primarily because it is most reliable and little susceptible to disturbances. Even when the surgeon covers a part of the eye with an instrument already at the start of the method, the radius can be reliably found because the ring-shaped character of the limbus or the pupil edge is further retained as long as the eye is not fully covered.

An especially reliable rapid and advantageous method for localizing ring-shaped characteristic eye components such as the limbus or the pupil edge is comprised of performing a convolution of the image with a ring-shaped comparison object which is made up of two concentric ring-shaped components between which a difference formation takes place with the convolution. Because the comparison object or the filter has at least two components, the possibility results to adapt one component to the eye region outside of the brightness transition (for example, the sclera) and to adapt the second component to the eye region which lies within the brightness transition (for example, the iris).

With these two components, the brightness transition can be intensified to a certain extent via the convolution with the filter. The optimal coincidence with the template or filter which is used depending upon the method, results when the inner ring of the comparison object lies, for example, on the iris and the outer ring, for example, lies on the sclera and the transition region, that is, in the case of the limbus, is therewith enclosed by the two ring-shaped components. The limbus center thereby comes into coincidence with the center of the comparison object.

Here it is noted that it is not absolutely necessary to select the maximum of the filter response as the limbus center or pupil center. It could also be purposeful to take a point in the proximity of the maximum if it has been shown, for example, by including other criteria, that this point more likely corresponds to the center.

Although the ring-shaped configuration of the comparison object is basically important for the method, it would not change anything important in the method if a polygon, a disc or the like were used. It is also not necessary that a closed ring be used. The comparison object can be put together from ring-shaped segments. What is significant for the method is only that, in total, the ring-shaped character of the comparison object is retained. Especially in the edge region of the image, it is even better to use only ring segments. With these ring segments, that region is preferably omitted which lies at the edge whereat the comparison object approaches during the correlation and therewith also the limbus in the image. In this way, the comparison object better corresponds in a correlation to the object to be found which is likewise partially cropped as soon as it arrives at the edge region of the image.

This method has proven to be especially advantageous for the analysis of the further recordings of the eye detail which take place in almost real time because the method can be carried out very rapidly with the input of a known radius for the comparison object which is to be correlated and because of the particular averaging which permits each determination of a ring-shaped object as soon as only the ring-shaped character is somewhat visible. Even when part of the ring is covered, it has been shown to be most reliable especially in the later course of the surgery wherein many procedures of the surgeon are necessary and therefore many disturbance quantities affect the limbus.

The use of a radius, which is derived in a first localization method, in all further tracking methods wherein the same characteristic eye component is intended to be determined in the eye detail, can, however, also be used very advantageously when one operates, for example, with an edge detection method. After the determination of all relevant edges, a Hough transformation often follows wherein ring-shaped objects are found in an image which is binarized based on an edge detection. The known radius can be used to check whether the ring-shaped object determined on the basis of the Hough transformation also actually corresponds to the eye component to be looked for. For this reason, this method is not accelerated but is at least made more reliable in lieu thereof.

In a further embodiment of the method, the color channel is determined as a characteristic quantity especially in the recording of multicolor digital images. This color channel is the most suitable for carrying out the localization of the eye component in the subsequent method. It is important to select a color channel which as gray scale image becomes the basis of the localization method for accelerating the method by means of data reduction as well as for increasing the reliability of the method. The particular suitable color channel is in general that color channel wherein the sought characteristic eye component, that is, for example, the limbus or the pupil edge, has the greatest brightness transition, that is, the greatest jump in contrast. This can also be a combination of several color channels. This jump in contrast is dependent from the iris color as well as being dependent from the color of the sclera as well as the effect caused by the surgery or the illuminating conditions.

After one has determined the information as to the characteristic eye component from the image, it can be determined which color channel is the best suited for determining this quantity in precisely this image. In an advantageous manner, this color channel is then likewise utilized for all further localizations of the characteristic eye component in the subsequent method and in the analysis of all further recordings. It can be assumed that this color channel is also very suitable for the subsequent recordings. For this reason, it is not necessary to determine the color channel for each image. In this way, the speed of each utilized subsequent method is significantly increased. Independently of which algorithm is used, it is therefore easier to ensure a real time analysis.

In a further advantageous embodiment of the invention, the characteristic quantity, which is determined after the one-time localization of the characteristic eye component and is used again and again in the further method, is a threshold value. Fixing absolute threshold values for the binarization or segmentation of a digital image is always extremely critical and errors are often associated therewith. It is always like walking a tightrope between retaining too much data and the elimination of data important for the evaluation especially for the large, differences which are present between eyes per se and especially between diseased eyes. Sometimes the iris is very bright and the pupil very dark or almost black. At another time, the pupil is bright or milky because of a cataract and the iris can be dark brown or almost black. There are even cases wherein the iris and pupil are of almost the same color. Especially for these recordings, the determination of an absolute threshold value is extremely prone to errors and difficult. For this reason, it is very advantageous to so derive a purposeful threshold value that, in a first localization step, one can work especially accurately and therefore time intensively in order to reliably find the characteristic eye feature and from this to take a threshold value suitable for the processing of all further images in extremely short processing time.

In the context of the method of the invention, it can, for example, be advantageous to find, for example, the boundary between the sclera and the iris or the boundary between the iris and the pupil in the first time localization of a characteristic eye component in that the digital image of the eye detail is binarized based on an edge detection method and to determine two circles lying one within the other in the binary image via a Hough transformation. In the event that the threshold value for the edge detection is carefully selected, the Hough transformation is a very suitable means to reliably find the two transitions and based upon this, to then derive the center of the iris or pupil. However, carrying out Hough transformations is time intensive and therefore not suitable to rapidly analyze all images which are recorded in the course of an eye examination or eye treatment so that thereafter in each approximately the same image of the eye, an assist can be faded in. For this reason, for the subsequent method, that is, for determining the position of the characteristic eye components in the following recording, another method is advantageously used. In the color component, wherein the mean values of pupil and iris differ the most, that is, wherein the contrast between them is the highest, a threshold value is defined which lies between the two mean values. In all subsequent images, the pupil is separated from the iris and therewith the pupil is determined based on threshold value formation in order to determine its center. This method can likewise be used for the boundary between sclera and iris. What is important only is that the threshold value, which is used for the threshold value formation, is derived from the first method step wherein the characteristic eye feature is determined by means of a Hough transformation and that this threshold value is retained for the further recordings. With this method too, it is possible to ensure a reliable and, at least for all subsequent recordings, a rapid localization of the characteristic eye components.

What is important for the method of the invention is that the recording conditions between localization method and subsequent method remain the same or that changes, in the event that they occur, are known. For this reason, in a further especially advantageous embodiment, the characteristic quantity, which is used for all further recordings, is always preferably automatically adapted when the recording conditions on the camera are changed. Thus, for example, the radius is always correspondingly adapted when the zoom factor on the camera is changed. For this purpose, it is necessary to make an interface available between the camera and the evaluation unit. Also, the selection of the color channel or the threshold value might have to be adapted when the recording mode of the camera is changed. If, for example, the illumination or the sensitivity of the camera is changed, then this has an intense effect on the contrast relationships. In this case, it is very advantageous to undertake an adaptation. This adaptation can also take place in that the localization method is carried out which is more time intensive and a new radius, threshold value or color channel is selected. This interrupts, however, the method and leaves the surgeon without an assist for a while.

It is understood that the foregoing description is that of the preferred embodiments of the invention and that various changes and modifications may be made thereto without departing from the spirit and scope of the invention as defined in the appended claims.

What is claimed is:

1. A method for determining the position and/or radius of the limbus and/or the position and/or radius of the pupil of a patient eye, the method comprising the steps of:
    obtaining an image of the patient eye;
    providing a plurality of different ring-shaped comparison objects having respective radii and respective centers;
    correlating said image with said plurality of said comparison objects to yield a local best match between said image and said comparison objects when there is a coincidence of one of said ring-shaped comparison objects and a ring-shaped jump in brightness in said image having the same radius and the same center;
    determining said comparison objects having a local best match with said image;
    selecting the position of the center of the comparison object having a local best match with said image as the position of the center of the limbus and/or the position of the center of the pupil;
    said ring-shaped comparison objects being closed ring filters or part ring filters; and,
    a filter response (A) of said ring filters being computed for said image of the patient eye as a measure for the correlation of said image of the patient eye and said ring filters;
    wherein a local maximum filter response (A) is determined with respect to said ring filters; and, the position of the center and the radius of the ring filter, on which said filter response (A) is based, is selected as the position of the center of the limbus of the patient eye and as the radius of the limbus; and/or, as the position of the center of the pupil of the patient eye and the radius of the pupil.

2. A method for determining the position and/or radius of the limbus and/or the position and/or radius of the pupil of a patient eye, the method comprising the steps of:
    obtaining an image of the patient eye;
    providing a plurality of different ring-shaped comparison objects having respective radii and respective centers;
    correlating said image with said plurality of said comparison objects to yield a local best match between said image and said comparison objects when there is a coincidence of one of said ring-shaped comparison objects and a ring-shaped jump in brightness in said image having the same radius and the same center;
    determining said comparison objects having a local best match with said image;
    selecting the position of the center of the comparison object having a local best match with said image as the position of the center of the limbus and/or the position of the center of the pupil;
    said ring-shaped comparison objects being closed ring filters or part ring filters;
    a filter response (A) of said ring filters being computed for said image of the patient eye as a measure for the correlation of said image of the patient eye and said ring filters; and,
    each of said ring filters comprising an inner filter ring and an outer filter ring;
    wherein the radius of said inner filter ring is smaller than the radius of the pupil of the patient eye and the radius of the outer filter ring is greater than the radius of the pupil of the patient eye; or, the radius of the inner filter ring is smaller than the radius of the limbus of the patient eye and the radius of the outer filter ring is greater than the radius of the limbus of the patient eye.

3. The method of claim 1, wherein said filter response (A) is computed in a computer unit via a convolution of a digital image of the patient eye with a filter function for said ring filters; and, said computer unit determines a filter function having at least one local maximum filter response from the computed filter responses.

4. The method of claim 3, wherein the radius of the ring filter having the local maximum filter response is selected as the radius of the pupil or the limbus of the patient eye; and, the position of the center of said ring filter is selected as the position of the center of the pupil or of the limbus of the patient eye.

5. The method of claim 4, wherein the ring-shaped comparison object is a ring filter; and, the criterion for the local best match with the image of the patient eye is an at least local maximum filter response of the ring filter for the image of the patient eye and for the reference image.

6. The method of claim 5, wherein a quantity (Z) is generated as a measure for the reliability of a determined radius of the pupil and/or of the limbus of the patient eye and/or of a determined position of the center of the pupil and/or of the limbus of the patient eye from the deviation of the measure for the correlation of the image of the patient eye from the measure for the correlation of a reference image with the comparison object.

7. The method of claim 6, wherein said measure for the reliability is indicated by an indicator unit.

8. The method of claim 7, wherein the indication is effected acoustically or optically.

9. The method of claim 8, wherein the indication is reflected into the optical beam path.

10. An ophthalmologic visualization system for eye surgery, the system comprising:
    an apparatus for determining the position and/or radius of the limbus and/or the position and/or radius of the pupil of a patient eye;
    means for obtaining an image of the patient eye;
    a plurality of different ring-shaped comparison objects having respective radii and respective centers;
    means for correlating said image with said plurality of said comparison objects to yield a local best match between said image and said comparison objects when there is a coincidence of one of said ring-shaped comparison objects and a ring-shaped jump in brightness in said image having the same radius and the same center;

means for determining said comparison objects having a local best match with said image; and, means for selecting the position of the center of the comparison object having a local best match with said image as the position of the center of the limbus and/or the position of the center of the pupil;

wherein said ring-shaped comparison objects are closed ring filters or part ring filters; said closed ring filters or part ring filters have an inner filter ring and an outer filter ring; and, a measure for the correlation of the image of the patient eye and said comparison objects is determined by computing the filter response of a ring filter for the image of the patient eye; and, wherein the inner and outer filter rings of said ring filter each contribute to said filter response with a different sign.

11. An ophthalmologic visualization system for eye surgery, the system comprising:

an apparatus for determining the position and/or radius of the limbus and/or the position and/or radius of the pupil of a patient eye;

means for obtaining an image of the patient eye;

a plurality of different ring-shaped comparison objects having respective radii and respective centers;

means for correlating said image with said plurality of said comparison objects to yield a local best match between said image and said comparison objects when there is a coincidence of one of said ring-shaped comparison objects and a ring-shaped jump in brightness in said image having the same radius and the same center;

means for determining said comparison objects having a local best match with said image;

means for selecting the position of the center of the comparison object having a local best match with said image as the position of the center of the limbus and/or the position of the center of the pupil;

said ring-shaped comparison objects being closed ring filters or part ring filters; said filter having an inner filter ring and an outer filter ring; and, a measure for the correlation of the image of the patient eye and said comparison objects being determined by computing the filter response of a ring filter for the image of the patient eye;

wherein a first measure (A) for the correlation of the image of the patient eye and of the comparison object in the form of the ring filter having an at least local maximum filter response is compared to a second measure for the correlation of a reference image and a comparison object in the form of a ring filter having an at least local maximum filter response; a quantity (Z) is generated from the deviation of the first measure from the second measure with said quantity (Z) being a measure for the reliability of a determined radius of the pupil or of the limbus of the patient eye or a determined position of the center of the pupil or of the limbus of the patient eye; and, said quantity (Z) is indicated by an indicating unit.

* * * * *

UNITED STATES PATENT AND TRADEMARK OFFICE
CERTIFICATE OF CORRECTION

PATENT NO.         : 8,662,667 B2                                    Page 1 of 1
APPLICATION NO.    : 12/801689
DATED              : March 4, 2014
INVENTOR(S)        : T. Schuhrke et al.

It is certified that error appears in the above-identified patent and that said Letters Patent is hereby corrected as shown below:

In the Specification

In Column 1:
Line 16: delete "DE i0" and substitute -- DE 10 -- therefor.
Line 16: delete "(b) DE i0" and substitute -- (b) DE 10 -- therefor.
Line 16: delete "(c) DE i0" and substitute -- (c) DE 10 -- therefor.
Line 17: delete "(d) DE i0" and substitute -- (d) DE 10 -- therefor.
Line 17: delete "(e) DE i0" and substitute -- (e) DE 10 -- therefor.

In Column 5:
Line 16: delete "oomparison" and substitute -- comparison -- therefor.

In Column 15:
Line 36: delete "Correlation" and substitute -- correlation -- therefor.

In Column 22:
Line 16: delete "large, differences" and substitute -- large differences -- therefor.

Signed and Sealed this
Twenty-fourth Day of June, 2014

Michelle K. Lee
*Deputy Director of the United States Patent and Trademark Office*